US008669263B2

(12) United States Patent
Lemke et al.

(10) Patent No.: US 8,669,263 B2
(45) Date of Patent: *Mar. 11, 2014

(54) USE OF TAM RECEPTOR INHIBITORS AS ANTIMICROBIALS

(71) Applicant: The Salk Institute for Biological Studies, La Jolla, CA (US)

(72) Inventors: Greg E. Lemke, La Jolla, CA (US);
John A. T. Young, San Diego, CA (US);
Carla V. Rothlin, New Haven, CT (US);
Suchita Bhattacharyya, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/790,191

(22) Filed: Mar. 8, 2013

(65) Prior Publication Data

US 2013/0251734 A1    Sep. 26, 2013

Related U.S. Application Data

(63) Continuation of application No. 12/741,812, filed as application No. PCT/US2008/082902 on Nov. 7, 2008, now Pat. No. 8,415,361.

(60) Provisional application No. 60/986,984, filed on Nov. 9, 2007, provisional application No. 61/013,598, filed on Dec. 13, 2007, provisional application No. 61/083,462, filed on Jul. 24, 2008.

(51) Int. Cl.
*C07D 471/04* (2006.01)
*A61K 31/41* (2006.01)

(52) U.S. Cl.
USPC .......................... 514/257; 514/359; 514/383

(58) Field of Classification Search
USPC .......................................... 514/257, 359, 383
See application file for complete search history.

(56) References Cited

U.S. PATENT DOCUMENTS 6,255,068 B1   7/2001  Godowski et al.
6,635,416 B2  10/2003  Palese et al.

2005/0245524 A1  11/2005  Noronha et al.
2007/0213375 A1   9/2007  Singh et al.
2007/0259904 A1  11/2007  Noronha et al.

FOREIGN PATENT DOCUMENTS

WO      WO 89/02922 A1    4/1989
WO      WO 2004/046120 A2  6/2004
WO      WO 2005/037825 A2  4/2005

OTHER PUBLICATIONS

Camenisch et al., "A Novel Receptor Tyrosine Kinase, Mer, Inhibits TNF-α Production and Lipopolysaccharide-Induced Endotoxic Shock," *J. Immunol.* 162:3498-3503, 1999.
Chan et al., "Induction of Interferon γ Production by Natural Killer Cell Stimulatory Factor: Characterization of the Responder Cells and Synergy with Other Inducers," *J. Exp. Med.* 173:869-879, 1991.
Lu et al., "Homeostatic Regulation of the Immune System by Receptor Tyrosine Kinases of the Tyro 3 Family," *Science* 293:306-311, 2001.
O'Neill, "TAMpering with Toll-Like Receptor Signaling," *Cell* 131:1039-1041, 2007.
Rothlin et al., "TAM Receptors Are Pleiotropic Inhibitors of the Innate Immune Response," *Cell* 131:1124-1136, 2007.
Rothlin and Lemke, "TAM Receptor Signaling in Dendritic Cells Negatively Regulates the Innate Immune Response" Immunology Gordon Conference, Ventura California, Presentation on Mar. 27, 2007.
Sasaki et al., "Structural Basis for Gas6-Axl Signalling," *EMBO J.* 25:80-87, 2006.
Scott et al., "Phagocytosis and Clearance of Apoptotic Cells is Mediated by MER," *Nature* 411:207-211, 2001.
Shimojima et al., "The Mechanism of Axl-Mediated Ebola Virus Infection," *JID* 196:S259-S263, 2007.
Williams et al., "TAM Receptors are Dispensable in the Phagocytosis and Killing of Bacteria," *Cell. Immunol.* 259:128-134, 2009.
Dai and Siemann, "BMS-777607, a Small-Molecule Met Kinase Inhibitor, Suppresses Hepatocyte Growth Factor—Stimulated Prostate Cancer Metastatic Phenotype In vitro," *Mol. Cancer Ther.* 9:1554-1561, 2010.

*Primary Examiner* — Renee Claytor
(74) *Attorney, Agent, or Firm* — Klarquist Sparkman, LLP

(57) ABSTRACT

This disclosure concerns antimicrobial compositions and methods for immunoenhancement, for example methods of increasing production of a type I interferon (IFN) in response to pathogen infection, by administration of a TAM receptor inhibitor. In certain embodiments, the disclosure concerns methods of using a TAM receptor inhibitor to treat a viral or bacterial infection in a subject.

10 Claims, 4 Drawing Sheets

FIG. 3

IFNβ induction: Ebola pseudotype

IFNβ induction: VSV pseudotype

US 8,669,263 B2

USE OF TAM RECEPTOR INHIBITORS AS ANTIMICROBIALS

CROSS REFERENCE TO RELATED APPLICATION

This application is a continuation of U.S. application Ser. No. 12/741,812, filed on May 6, 2010, now U.S. Pat. No. 8,415,361, which is the U.S. National Stage of International Application No. PCT/US2008/082902, filed Nov. 7, 2008, which was published in English under PCT Article 21(2), which in turn which claims the benefit of U.S. Provisional Application No. 60/986,984, filed on Nov. 9, 2007, U.S. Provisional Application No. 61/013,598, filed on Dec. 13, 2007, and 61/083,462 filed on Jul. 24, 2008 each of which is incorporated herein by reference in its entirety.

FIELD OF THE DISCLOSURE

This disclosure concerns compositions and methods for using a Tyro3, Axl, and Mer (TAM) receptor inhibitor for immunoenhancement, such as in the treatment of chronic and acute viral and bacterial infections.

BACKGROUND

Viral and bacterial infections are a major threat to public health. The emergence and expansion of life-threatening diseases caused by viruses and bacteria (e.g., acquired immune deficiency syndrome, severe acute respiratory syndrome, West Nile and Ebola hemorrhagic fevers, and tuberculosis), together with unmet conventional prevention approaches (e.g., vaccines) highlights the necessity of exploring new strategies that target these deadly pathogens.

Recent studies have revealed that the TAM (Tyro3, Axl and Mer) tyrosine kinase receptors are positioned and function at a critical node of the innate immune response (Rothlin et al., Cell, 2007. 131(6):1124-36; Lemke and Rothlin, Nat. Rev. Immunol., 2008. 8(5):327-36). They are induced in dendritic cells (DCs) and macrophages by Type I interferon (IFN) receptors, which are themselves engaged as a consequence of toll-like receptor (TLR) activation upon encounter with pathogens (e.g., viruses and bacteria). The TAMs then act in concert with type IFN receptors to inactivate both the type I IFN receptors themselves, as well as the TLRs that initially trigger the inflammatory response to pathogens. In this way, the TAMs act as both pleiotropic inhibitors and integrated components of the innate immune response.

The innate immune system fights infection by viruses and bacteria in part through the production of Type I interferons (IFNs), a family of 13 alpha interferons and a single beta interferon (Borden et al., Nat. Rev. Drug Discov., 2007. 6(12): 975-90). These agents display broad antiviral and antibacterial activities.

Given the foregoing, it would be desirable to have improved immunoenhancing agents, for instance for use in treating pathogen infections.

SUMMARY OF THE DISCLOSURE

The inventors have surprisingly found that inhibition of the TAM pathway in virally infected macrophages from TAM triple knock out (TKO) mice leads to reduced levels of infection with a variety of pseudotyped viruses with either filoviral, retroviral, or rhabdoviral glycoproteins (GPs). These virus particles triggered much higher levels of type I interferon (IFN) production in cells from TKO mice than from wild type (WT), indicating that viral interaction with the TAM pathway acts normally to dampen this antiviral response. Consistently, viral infectivity in 293 cells was increased upon stable overexpression of Tyro3. These results are inconsistent with a specific role for TAM receptors during filovirus entry and instead indicate that viruses may have co-opted the TAM pathway to interfere with innate immune processes mounted by the host. These results indicate that the TAM receptors normally facilitate virus and also likely bacterial infectivity by inhibiting IFN production, and indicate that TAM receptor inhibitors can be therapeutically useful as anti-microbial compounds.

Methods are provided for enhancing an immune response in a subject, for example enhancing a pro-inflammatory cytokine (e.g., type I IFN) response against a pathogen in a subject. In some examples, the method includes administering to a subject infected with a pathogen (e.g., virus, bacteria, fungus, parasite, or combinations thereof) a therapeutically effective amount of a TAM receptor inhibitor, thereby enhancing the immune response against the pathogen, such as enhancing a type I interferon response (e.g., increasing IFN-alpha (IFN-α) or beta (IFN-β) production in macrophages or other cells that express TAM receptor and IFN-α or IFN-β). In some examples the pathogen includes an HIV viral vector pseudotyped with Ebola or Marburg or vesicular stomatitis virus (VSV) or murine leukemia virus (MLV) ampho envelope proteins. In particular examples, the pathogen is not a filovirus. In some examples, such methods treat or prevent a pathogen infection.

In a specific example, the disclosure provides methods of treating a viral (which in some examples is not a filovirus) or bacterial infection in a subject, for example by enhancing an immune response, such as a type I IFN response (e.g., increasing IFN-α or IFN-β). For example, the method can include administering to a subject infected with or suspected of being infected with a virus (e.g., an enveloped virus) or bacteria, a therapeutically effective amount of a TAM receptor inhibitor, thereby treating the infection.

The disclosure also provides methods of screening to identify antimicrobial (e.g., anti-viral or anti-bacterial) agents. In particular examples the methods include contacting a cell that expresses a TAM receptor with one or more test agents and with an amount of pathogen sufficient to infect the cell, then measuring secretion or production of a type I IFN (such as IFN-α or IFN-β) or interferon response factors (IRF) such as IRF3, 5 and 7 which are direct transducers of virus-mediated signaling (Nakaya et al, Biochem. Biophys. Res. Commun., 2001. 283(5):1150-6; Yanai et al, PNAS, 2007. 104(9):3402-7) by the cell, wherein an increase in type I IFN production or IRF production by the cell (for example relative to an infected cell no treated with the test agent) indicates that the test agent is an antimicrobial agent.

The foregoing and other features will become more apparent from the following detailed description of several embodiments, which proceeds with reference to the accompanying figures.

BRIEF DESCRIPTION OF THE FIGURES

FIG. 3 is a bar graph showing levels of IFN-β production by WT or TKO macrophages challenged with retroviral vector carrying the Ebola or VSV glycoproteins. Challenge of WT macrophages with pseudotyped viruses carrying Ebola (left panel) or VSV (right panel) envelope glycoproteins leads to 3 and 8-fold elevation in IFN-β, respectively, at 4 hours post-challenge. In marked contrast, challenge of TAM-deficient macrophages with the same viruses results in 55-fold and 45-fold elevations in IFN-β at 4-hours post-challenge.

SEQUENCE LISTING

Figure 1:
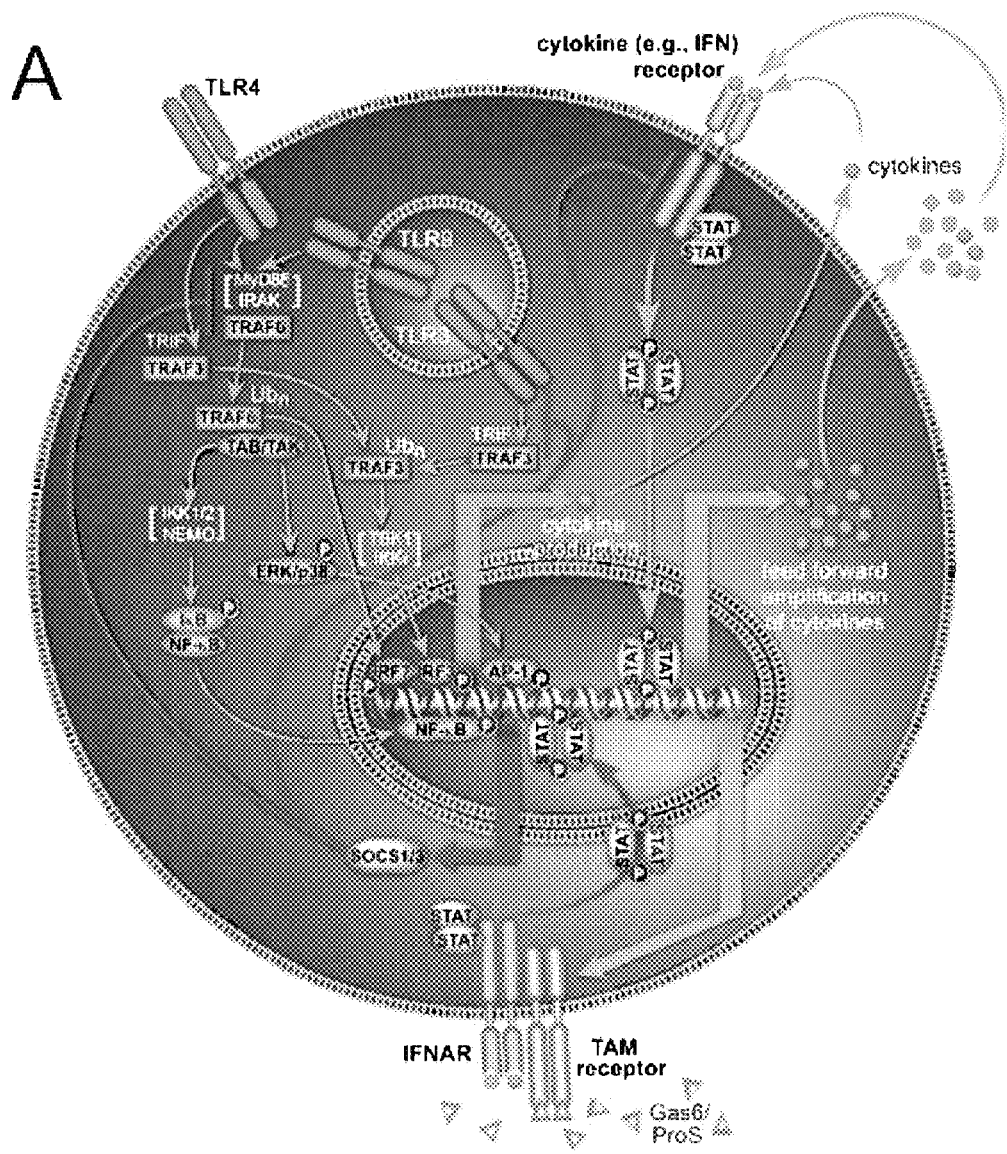
FIG. 1 is a schematic drawing showing the sequential engagement of the TAMs. Bacteria and viruses are recognized by pattern recognition receptors such as the TLRs (for example, TLR3/4/9) expressed by dendritic cells (DCs) and macrophages, which activate a signal transduction cascade that results in the initial production of type I IFNs and other cytokines. The levels of these cytokines are then greatly amplified in a feed forward loop through cytokine receptor signal transduction pathways. These pathways in turn activate the expression of TAM receptors, whose own signal transduction pathway results in the expression of SOCS proteins, which shut down TLR and IFN receptors, and thus, the innate inflammatory response.

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand.

SEQ ID NOS: 1 and 2 are primers used to detect HIV early reverse transcriptase products.

SEQ ID NO: 3 is a fluorescently-labeled probe used to detect HIV early reverse transcriptase products.

SEQ ID NOS: 4 and 5 are forward and reverse primers, respectively, used to detect IFN-β using PCR.

DETAILED DESCRIPTION

I. Overview of Several Embodiments

A previously published report concluded that TAM family members are required specifically for entry of Ebola and Marburg viruses into cells (Shimojima et al., *J. Virol.*, 80(20): 10109-16, 2006). To determine the specificity of TAM family members for filovirus infection and to characterize the step in viral replication cycle that is affected by TAM family members, the inventors compared infectivity of HIV vectors pseudotyped with either Ebola, Marburg, vesicular stomatitis virus (VSV) or murine leukemia virus (MLV) ampho envelope glycoproteins in macrophages from TAM (Tyro3, Axl, and Mer) triple knockout (TKO) mice. Disclosed herein are methods that take advantage of the surprising discovery that macrophages having deletion of the TAM receptor (prepared from TAM TKO mice) show decreased infectivity by all of these viruses when compared to infectivity of macrophages from wild-type (WT) mice. These viruses also potentiate Type I interferon (IFN) production in TKO cells, representing a significant enhancement in this antiviral response over that seen with WT cells. Based on these observations, the disclosure provides methods using TAM receptor inhibitors as antimicrobials, for example to treat pathogen infections, such as acute and chronic viral, bacterial, fungal, and parasitic infections.

In one example, methods are provided that enhance a pro-inflammatory cytokine (e.g., type I IFN) response against a pathogen in a subject. In some examples, such methods are used to treat a viral, bacterial, fungal or parasitic infection in a mammalian subject. For example, the method can include administering to a pathogen-infected subject (or a subject suspected of being infected with a pathogen or who is likely to become infected with a pathogen in the near future) a therapeutically effective amount of a TAM receptor inhibitor, thereby enhancing the type I interferon response against a pathogen in the subject. Such a type I interferon response can be an increase in the production of a pro-inflammatory cytokine, such as a type I IFN (e.g., IFN-α or IFN-β) by a cell (for example a cell that expresses TAM receptor, for example an immune cell, such as a macrophage or DC, fibroblast or cardiomyocyte). In some examples, the increase is an at least 20-fold increase (such as an at least 40-fold or at least 50-fold) relative to a control or reference value (or range of values). Exemplary controls/reference values include the expected response in the absence of the TAM receptor inhibitor (e.g., an amount or range of amounts of type I IFN (such IFN-α or IFN-β) expected to be produced in the absence of treatment with the TAM receptor inhibitor).

In some examples, the method can further include measuring production of one or more type I IFNs or interferon response factors (IRFs), such as measuring IFN-α, IFN-β, IRF3, IRF5, and/or IRF7 production. For example, a biological sample from the subject can be analyzed for levels of type I IFN (such IFN-α or IFN-β) and/or the levels of one or more IRFs. Such methods are routine in the art. For example a blood sample that includes immune cells (e.g., macrophages or DCs) can be analyzed for relative or absolute amounts of type I IFNs (such IFN-α or IFN-β) or interferon response factors (IRFs), such as IRF3, 5 and 7. For example, type I IFN and IRF proteins can be detected using an ELISA or other routine protein-detection method and mRNA levels can be measured by qPCR using appropriate probes and/or primers. In some examples, the subject is monitored for one or more signs or symptoms of a pathogen infection, such as fever, chills, headache, lethargy, vomiting, coughing, and the like. In some examples the subject also receives a therapeutically effective amount of one or more other anti-infectious agents, such as anti-viral or antibiotic agents. In some examples, the TAM receptor inhibitor is administered to the subject before, substantially concurrently with, or after the other anti-infectious agent.

In some examples, subjects are treated with a TAM receptor inhibitor for a short period of time, to avoid or reduce complications that may result from chronic administration of a TAM receptor inhibitor. For example, subjects can be treated for a period of less than 30 days, such as less than 14 days, less than 7 days, less than 3 days, or less than 2 days. In some examples, subjects are treated for 1 to 2 days, 1 to 3 days, 3 to 7 days, 3 to 14 days, or 7 to 14 days.

In some examples, subjects are treated with a TAM receptor inhibitor for longer periods of time, but under conditions that avoid or reduce complications that may result from chronic administration of a TAM receptor inhibitor. For example, subjects can be treated with lower concentrations of a TAM receptor inhibitor such that sufficient but not permanent inhibition of the receptor is achieved. In some examples, a dose of less than the $IC_{50}$ for the TAM receptor inhibitor is administered, such as at least 10% less, at least 20%, or at least 50% less than the $IC_{50}$, for example for a period of at least 30 days, at least 60 days, at least 120 days, or at least 200 days.

In certain examples of the method, the TAM receptor inhibitor is a Tyro3, Axl, or Mer inhibitor. In particular examples, the TAM inhibitor is a small molecule inhibitor of the receptor's tyrosine kinase (enzymatic) activity, an antibody that blocks TAM receptor activation or TAM receptor-ligand interaction, a siRNA (or other inhibitory RNA molecule) that lowers Tyro3, Axl, or Mer expression levels in DCs, macrophages, and other TAM receptor-positive cells, or any other agent that lowers TAM receptor ligand concentration (such as decreasing Protein S and or Gas6 levels, for example using Protein S or Gas6 specific siRNA or antibodies). For example, the TAM receptor inhibitor can be a membrane-permeable small molecule that specifically binds to and inhibits a TAM receptor intracellular kinase domain, such as the ATP binding site of Tyro3, Axl, or Mer. In another example, the TAM receptor inhibitor specifically binds to an extracellular domain of the TAM receptor, thereby interfering with the binding of a ligand (e.g., Gas6 or Protein S) to the TAM receptor. In yet another example, the TAM receptor inhibitor specifically binds to a TAM receptor ligand (e.g., Gas6 or Protein S) thereby interfering with the binding of the ligand to the receptor. Inhibitors that specifically bind to the TAM receptor extracellular domain or a ligand of the TAM receptor (e.g., an antibody, such as an anti-Gas6 or anti-Protein S antibody) can significantly reduce or inhibit the interaction of the ligand with the receptor or block activation of the receptor. In yet other examples, the TAM receptor inhibitor is an RNAi (such as an siRNA or shRNA) specific for Tyro3, Axl, or Mer, thereby decreasing expression and activity of TAM receptors. In certain particular examples, a TAM inhibitor has an $IC_{50}$ of less than about 50 µM (such as less than about 10 µM, less than about 1 µM, less than about 0.1 µM, less than about 1 nM, or less than about 1 pM) and in even more particular examples, the TAM inhibitor has an $IC_{50}$ of from about 0.005 µM to about 5 µM, from about 1 nM to about 5 µM, from about 100 pM to about 5 nM, or from about 0.1 pM to about 10 µM.

In yet more particular examples, the TAM inhibitor is MP470 (see for example Mahadevan et al., *Oncogene* 26(27): 3909-19, 2007), SGI-AXL-277 (a pyrrolopyrimidine), AXL-1, AXL-2, AXL-3, AXL-4, AXL-5, AXL-6, AXL-7, AXL-8, or AXL-9 (all available from Supergen Inc., Dublin, Calif.), as well as derivatives thereof. Other small molecule TAM receptor inhibitors can be obtained, for example, from Rigel Pharmaceuticals, Inc., San Francisco, Calif. and SuperGen, Inc., Dublin, Calif. Other specific examples of TAM receptor inhibitors can be found in PCT Publication Nos: WO07030680A3, WO06052936A3, WO04092735A3, WO07056151A2, and U.S. Patent Publication No: US20070142402 (all hereby incorporated by reference). In some examples, the AXL inhibitor is a triazole derivative. Examples of AXL inhibitors are disclosed in U.S. Patent Publication 2007/0213375, filed Sep. 13, 2007, which is incorporated herein by reference in its entirety. In certain examples, the AXL inhibitor is a triazole derivative with one of the following general structures:

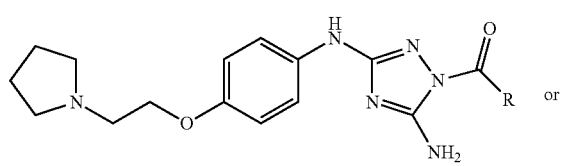

-continued

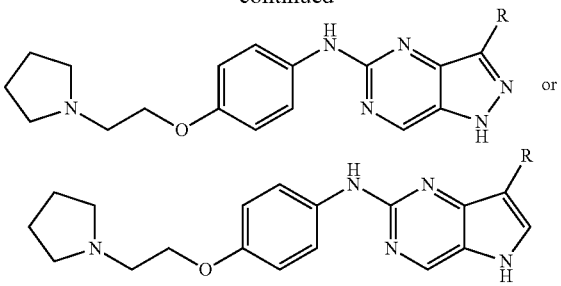

wherein R can be H or $CH_3$. Any pathogen can be treated with the disclosed methods including those that are regulatable by type I IFN (such as by increases in type I IFN production), such as those pathogens that interact with the TAM receptor during entry into a cell. Exemplary pathogens include "obligatory intracellular pathogens", which tend to immunosuppress the system to allow for pathogen persistence. In some examples, the subject is chronically infected with the pathogen. In other examples, the subject is acutely infected with the pathogen.

In a specific example, the pathogen is a virus, such as an enveloped virus. In some examples, the enveloped virus is not a filovirus (e.g., not Ebola or Marburg). Exemplary enveloped viruses include human immunodeficiency virus (HIV), murine leukemia virus (MLV), and vesicular stomatitis virus (VSV). Bacteria can also be treated with the disclosed methods. In some examples the bacterium is one that typically results in a chronic infection of the host, such as *Listeria monocyotgenes* or mycobacterium. In yet other examples, the pathogen is a parasite, such as *toxoplasma*. In some examples, the pathogen is a fungus, such as aspergillosis, candidiasis (thrush, yeast infection), coccidioidomycosis, cryptococcal meningitis, or histoplasmosis.

Also disclosed are methods of screening for an antimicrobial agent. These methods can include contacting (e.g., incubating or treating) a cell expressing a TAM receptor (e.g., Tyro3, Axl, or Mer) with a test agent and with a pathogen (e.g., virus, parasite, fungus, or bacterium) under conditions that permit the pathogen to infect the cell and that permit the test agent to specifically bind to the TAM receptor or its ligand, and determining whether the test agent increases type I IFN production by the cell. For example, type I IFN (e.g., IFN-α or IFN-β) production by the cell can be measured using routine cytokine-detection assays. In some examples of the method, determining whether the test agent increase type I IFN (e.g., IFN-α or IFN-β) production by the cell includes (a) determining a control level of type I IFN (e.g., IFN-α or IFN-β) production by the cell before contacting (e.g., incubating) the cell with the test agent, (b) contacting the cell with the test agent, and (c) determining whether contacting the cell with the test agent increases type I IFN (e.g., IFN-α or IFN-β) production by the cell as compared to the control level of type I IFN (e.g., IFN-α or IFN-β) production by the cell, wherein an increase in type I IFN (e.g., IFN-α or IFN-β) production by the cell (such as an increase of at least 10-fold, at least 20-fold or at least 50-fold) in the presence of the test agent relative to the control level indicates that the test agent is an antimicrobial. Similarly, in addition or in an alternative embodiment, IRF (e.g., IRF3, IRF5, or IRF7) production can be measured, wherein an increase in IRF production by the cell in the presence of the test agent relative to the control level indicates that the test agent is an antimicrobial. Exemplary cells that can be used include cells that can produce type I IFN upon pathogen infection and express TAM receptors (endogenously or exogenously). In a specific example, the cells are immune cells such as macrophages and DCs.

Certain embodiments of the method also include selecting a test agent indicated to be an antimicrobial agent for further analysis. In particular examples, the cell is in a laboratory mammal, and contacting the cell with the test agent includes administering the test agent to the mammal.

II. Abbreviations

AIDS acquired immunodeficiency syndrome
APC antigen-presenting cell
CMV cytomegalovirus
DC dendritic cell
ELISA enzyme-linked immunosorbent assay
FACS fluorescence-activated cell sorting
FIV feline immunodeficiency virus
GAS6 growth-arrest-specific protein 6
GP glycoprotein
HCV hepatitis C virus
HIB *Haemophilus influenzae* type B
HIV human immunodeficiency virus
HPV human papilloma virus
HSV herpes simplex virus
HZV herpes zoster virus
IFN interferon
IL interleukin
IRF interferon response factor
MLV murine leukemia virus
PCP *Pneumocystis Carinii* pneumonia
PS phosphatidylserine
PTK protein-tyrosine kinase
Q-PCR quantitative polymerase chain reaction
RIA radioimmunoassay
SHBG sex hormone binding globulin
SIV simian immunodeficiency virus
SOCS suppressor of cytokine signaling
TAM Tyro3, Axl, and Mer
TAM TKO TAM triple knockout
TLR Toll-like receptor
TNF tumor necrosis factor
VSV vesicular stomatitis virus
WT wild-type III. Terms In order to facilitate review of the various embodiments of the disclosure, the following explanations of specific terms are provided:

Administration: Introduction of an agent into a subject. Includes oral, rectal, vaginal, transdermal, and parenteral administration, for example administration of one or more TAM receptor inhibitors (alone or in combination with other agents). Generally, parenteral formulations are those that are administered through any possible mode except ingestion. This term also refers to injections, whether administered intravenously, intrathecally, intramuscularly, intraperitoneally, intra-articularly, or subcutaneously, and various surface applications including intranasal, inhalational, intradermal, and topical application, for instance.

Anti-infectious or anti-microbial agent: A substance (such as a chemical compound, protein, antisense or RNAi oligonucleotide, or other molecule) for use in treating a pathogenic infection of a subject. Anti-infectious agents include, but are not limited to, anti-fungal compounds, anti-viral compounds, and antibiotics. In a particular example, a TAM receptor inhibitor is an antimicrobial agent, for example an anti-viral or anti-bacterial agent. In some examples, a TAM receptor inhibitor is used in combination with other anti-fungal compounds, anti-viral compounds, antibiotics, or combinations thereof.

Antibiotics include, but are not limited to, amoxicillin, clarithromycin, cefuroxime, cephalexin ciprofloxacin, doxycycline, metronidazole, terbinafine, levofloxacin, nitrofurantoin, tetracycline, and azithromycin. Anti-fungal compounds include, but are not limited to, clotrimazole, butenafine, butoconazole, ciclopirox, clioquinol, clioquinol, clotrimazole, econazole, fluconazole, flucytosine, griseofulvin, haloprogin, itraconazole, ketoconazole, miconazole, naftifine, nystatin, oxiconazole, sulconazole, terbinafine, terconazole, tioconazole, and tolnaftate.

Anti-viral compounds include, but are not limited to, zidovudine, didanosine, zalcitabine, stavudine, lamivudine, abacavir, tenofovir, nevirapine, delavirdine, efavirenz, saquinavir, ritonavir, indinavir, nelfinavir, saquinavir, amprenavir, and lopinavir.

Anti-infectious agents also include hyper-immune globulin. Hyperimmune globulin is gamma globulin isolated from a donor, or from a pool of donors, that have been immunized with a substance of interest. Specifically, hyper-immune globulin is antibody purified from a donor who was repeatedly vaccinated against a pathogen.

Contact: To bring one agent into close proximity to another agent, thereby permitting the agents to interact. For example, a TAM receptor inhibitor can be added to cells in culture, thereby allowing the TAM receptor inhibitor to interact with an inhibit TAM receptors expressed by the cell. In another examples, cells in a mammal are contacted with a TAM receptor inhibitor by administration of the inhibitor to the subject.

Dendritic cell (DC): The principal antigen presenting cell (APC) involved in primary immune responses. Dendritic cells include plasmacytoid dendritic cells and conventional dendritic cells. Their major function is to obtain antigen in tissues, migrate to lymphoid organs and present the antigen in order to activate T cells, and express pro-inflammatory cytokines and chemokines (e.g., type I IFNs, IL-6, IL-12, TNFα) and that mobilize leukocytes and other immune cells to sites of infection and pathogen invasion. Immature DCs originate in the bone marrow and reside in the periphery as immature cells.

Detect: To determine if an agent (e.g., type I IFN) is present or absent. In some examples this can further include quantification. For example, use of an antibody specific for a particular protein (e.g., type I IFN or IRF) permits detection of the of the protein or protein-protein interaction in a sample, such as a sample treated with a TAM receptor inhibitor. In particular examples, an emission signal from a label is detected. Detection can be in bulk, so that a macroscopic number of molecules can be observed simultaneously. Detection can also include identification of signals from single molecules using microscopy and such techniques as total internal reflection to reduce background noise.

Enveloped virus: A virus having a viral envelope covering its protein capsid. Envelopes are typically derived from portions of the host cell membranes (phospholipids and proteins), but include some viral glycoproteins. Prior to infection, the viral envelope fuses with the host cell membrane, allowing the capsid and viral genome to enter and infect the host cell. Glycoproteins on the surface of the envelope serve to identify and bind to receptor components on the host's membrane.

Examples of enveloped viruses include, but are not limited to: influenza, Semliki Forest Virus (SFV), filoviruses (Ebola virus and Marburg virus), retroviruses (e.g., human immunodeficiency virus (HIV), simian immunodeficiency virus (SIV) or feline immunodeficiency virus (FIV)), rabies, Herpes simplex viruses (HSV), cytomegalovirus (CMV), Epstein Barr virus, murine leukemia virus (MLV), hepatitis C virus (HCV), human papillomavirus (HPV), coxsackie viruses, rhinoviruses, yellow fever virus, West Nile virus, and vesicular stomatitis virus (VSV).

Filoviruses: A family of viruses that belong to the order Mononegavirales. Filoviruses are single stranded negative-sense RNA viruses that target primates. There are two genera: the Ebola virus and Marburg virus. These viruses cause viral hemorrhagic fevers, characterized by bleeding and coagulation abnormalities, often leading to death.

HIV (human immunodeficiency virus): A retrovirus that causes immunosuppression in humans (HIV disease) and leads to a disease complex known as the acquired immunodeficiency syndrome (AIDS). Reference herein to "HIV" can include reference to the two species of HIV that infect humans, namely, HIV-1 and HIV-2, as well as subtypes thereof, as well as wild-type viruses and variants or mutants thereof. In some examples, the HIV is not a wild-type virus but is instead a mutant form. Mutant forms of HIV include, but are not limited to, those that are not replication-competent (e.g., have a functional deletion in the envelope gene), those having a mutant reverse transcriptase sequence (e.g., those that have a mutant RT sequence, such as those that are associated with NNRTI resistance for example L74V, V75I, A98G, L100I, K101E/D/C, K103N, V106A/M, V108I/M, E138K, Q145M, Y181C/I, Y188L/C/H, G190S/A/E, M230L, P225H, P236L, Y318F, N348I or combinations thereof)

"HIV disease" refers to a well-recognized constellation of signs and symptoms (including the development of opportunistic infections) in persons who are infected by an HIV virus, for example as determined by antibody or western blot studies. Laboratory findings associated with this disease include a progressive decline in T-helper cells.

$IC_{50}$: A measure of concentration used in pharmacology. $IC_{50}$, or the half maximal inhibitory concentration, represents the concentration of an inhibitor that is required for 50% inhibition of its target (for instance, an enzyme, a cell, a TAM receptor, or a microorganism). Generally, an $IC_{50}$ value is a measure of how much of a particular composition (e.g., a TAM receptor inhibitor) is needed to inhibit some biological process (e.g., a viral, fungal, parasitic, or bacterial infection) by 50%. $IC_{50}$ is commonly used as a measure of drug affinity, and represents the concentration of a composition that is required to obtain 50% of the maximum effect in vivo.

Immune response: A response of a cell of the immune system, such as a B cell or T cell or macrophage, to a stimulus (e.g., infection by a pathogen, such as a virus or bacteria). A "parameter of an immune response" is any particular measurable aspect of an immune response, including, but not limited to, cytokine secretion (IL-6, IL-10, IFN-α, IFN-β etc.), immunoglobulin production, dendritic cell maturation, and proliferation of a cell of the immune system. "Enhancing an immune response" includes the use of any composition or method that results in an increase in any of these parameters. One of skill in the art can readily determine an increase in any one of these parameters using known laboratory assays. In one specific non-limiting example, an ELISA is used to detect cytokine (e.g., IFN-β) secretion. A "substantial" increase in a parameter of the immune response is a significant increase in this parameter (e.g., in the presence of a TAM receptor inhibitor) as compared to a control (e.g., in the absence of a TAM receptor inhibitor). Specific, non-limiting examples of a substantial increase are at least about a 10-fold increase, at least about a 20-fold increase, at least about a 30-fold increase, at least about a 40-fold increase, at least about a 45-fold increase, at least about a 50-fold increase, and at least about a 55-fold increase.

One of skill in the art can readily identify a significant increase using known statistical methods. One, specific, non-limiting example of a statistical test used to assess a substantial increase is the use of a Z test to compare the percent of samples that respond to an activated TAM receptor (e.g., TAM receptor inhibitor absent) as compared to the percent of samples that respond to an inactivated TAM receptor (e.g., a TAM receptor inhibitor present). A non-parametric ANOVA can be used to compare differences in the magnitude of the response induced in the absence of a TAM receptor inhibitor as compared to the percent of samples that respond in the presence of a TAM receptor inhibitor. In this example, $p \leq 0.05$ is significant, and indicates a substantial increase in the parameter of the immune response. One of skill in the art can readily identify other statistical assays of use.

Interferon (IFN) type I: Interferons (IFNs) are cytokines produced by the immune cells of vertebrates in response to challenges by viruses (e.g., rhinovirus, influenza virus, HIV) as well as some parasites (e.g., *Leishmania*) and bacteria (e.g., *Listeria*). Type I IFNs bind to the cell surface receptor complex known as the IFN-α receptor, and exhibit pleiotropic effects on a wide variety of cell types, including antiviral activity and antibacterial, antiprozoal, immunomodulatory, and cell growth regulatory functions. For example, IFNs can inhibit viral replication within host cells, activate natural killer cells and macrophages, increase antigen presentation to lymphocytes, and induce the resistance of host cells to viral infection. Exemplary type I IFNs include the acid-stable interferons IFN-alpha (IFNα) and IFN-beta (IFN-β), as well as IFN-delta, IFN-omega, IFN-tau, and IFN-kappa. IFN-α and IFN-β are secreted by many cell types including lymphocytes (NK cells, B-cells and T-cells), macrophages, fibroblasts, endothelial cells, osteoblasts and others.

Interferon alpha (IFN-α): A type I interferon glycoprotein that is involved in the regulation of humoral immune responses and immune responses against viral infections. IFN-α is produced by leukocytes and other cells and stimulates macrophages in response to stimulation by live or inactivated virus and other agents and has antiviral activity.

There are at least 23 different IFN-alpha genes. They have a length of 1-2 kb and are clustered on human chromosome 9p22. Exemplary IFN-α sequences are known in the art, and are publicly available on GenBank or other databases, such as Genbank Accession Nos. AAA52716.1; NP_076918.1; NP_000596.2 (human proteins) and AAA37886.1; NP_996754.1 (mouse proteins) (sequences of which are herein incorporated by reference for the sequence available on Jul. 24, 2008).

Methods of detecting IFN-α production by a cell are known, and include real time quantitative PCR and ELISA.

Interferon beta (IFN-β): A type I interferon glycoprotein that is involved in the regulation of humoral immune responses and immune responses against viral and other pathogenic infections. IFN-β is produced by fibroblasts and other cells in response to stimulation by live or inactivated virus or by double-stranded RNA, and has antiviral, antiproliferative, and immunomodulating activity.

The human gene encoding IFN-β maps to chromosome 9p22 in the vicinity of the IFN-alpha gene cluster. Exemplary IFN-β sequences are known in the art, and are publicly available on GenBank or other databases, such as Genbank Accession Nos. AAC41702.1; NP_002167; CAH70160.1 (human proteins) and AAI19396.1; AAI19398.1 (mouse proteins)

(sequences of which are herein incorporated by reference for the sequence available on Jul. 24, 2008).

Methods of detecting IFN-β production by a cell are known, and include real time quantitative PCR and ELISA.

Interferon response factor (IRF): Transcription factors that regulate interferon (e.g., type I IFN) transcription. This family of proteins has diverse roles, including virus-mediated activation of interferon, and modulation of cell growth, differentiation, apoptosis, and immune system activity. Members of the IRF family are generally characterized by a conserved N-terminal DNA-binding domain containing tryptophan (W) repeats. Examples include interferon regulatory factor 3 (IRF3; OMIM: 603734), a transcription factor critical to the initiation of the antiviral response, IRF5 (OMIM: 607218), a mediator of toll-like receptor (TLR)7 signaling, and IRF7 (OMIM: 605047) which participates in the transcriptional activation of virus-inducible cellular genes. Exemplary IRF sequences are known in the art, and are publicly available on GenBank or other databases, such as Genbank Accession Nos. NP_001562 (protein) and NM_001571 (nucleic acid) (IRF3); NP_002191 and NM_002200 (nucleic acid) (IRF5); and NP_001563 (protein) and NM_001572 (nucleic acid) (IRF7) (sequences of which are herein incorporated by reference for the sequence available on Jul. 24, 2008).

Isolated: An "isolated" biological component (such as a nucleic acid molecule, peptide, or cell) has been purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression host cell for a recombinant peptide or nucleic acid molecule).

Pathogen: An organism that is able to evade the various normal defenses of a human or other mammalian host to cause infection, such as viruses, bacteria, parasites and fungi. In a particular example, a pathogen is one that can be treated with a TAM receptor inhibitor.

Examples of viruses that can be treated with the methods provided herein include, but are not limited to, enveloped viruses such as members of the following viral families: Retroviridae (e.g., HIV (such as HIV1 and HIV2), MLV, SIV, FIV, Human T-cell leukemia viruses 1 and 2, XMRV, and Coltiviruses (such as CTFV or Banna virus)); Togaviridae (for example, alphaviruses (such as Ross River virus, Sindbis virus, Semliki Forest Virus, O'nyong'nyong virus, Chikungunya virus, Eastern equine encephalitis virus, Western equine encephalitis virus, Venezuelan equine encephalitis virus) or rubella viruses); Flaviridae (for example, dengue viruses, encephalitis viruses (such as West Nile virus or Japanese encephalitis virus), yellow fever viruses); Coronaviridae (for example, coronaviruses such as SARS virus or Toroviruses); Rhabdoviridae (for example, vesicular stomatitis viruses, rabies viruses); Paramyxoviridae (for example, parainfluenza viruses, mumps virus, measles virus, respiratory syncytial virus, sendai virus, and metopneumovirus); Orthomyxoviridae (for example, influenza viruses); Bunyaviridae (for example, Hantaan virus, bunya viruses (such as La Crosse virus), phleboviruses, and Nairo viruses); Hepadnaviridae (Hepatitis B viruses); Herpesviridae (herpes simplex virus (HSV) 1 and HSV-2, varicella zoster virus, cytomegalovirus (CMV), HHV-8, HHV-6, HHV-7, and pseudorabies virus); Filoviridae (filoviruses including Ebola virus and Marburg virus) and Poxyiridae (variola viruses, vaccinia viruses, pox viruses (such as small pox, monkey pox, and Molluscum contagiosum virus), yatabox virus (such as Tanapox and Yabapox)). Non-enveloped viruses can also be treated with the methods provided herein, such as members of the following families: Calciviridae (such as strains that cause gastroenteritis); Arenaviridae (hemorrhagic fever viruses such as LCMV, Lassa, Junin, Machupo and Guanarito viruses); Reoviridae (for instance, reoviruses, orbiviruses and rotaviruses); Birnaviridae; Parvoviridae (parvoviruses, such as Human bocavirus adeno-associated virus); Papillomaviridae (such as papillomaviruses); Papovaviridae (papilloma viruses, polyoma viruses); Adenoviridae (adenoviruses); Picornaviridae (enteroviruses, enteric viruses, Poliovirus, coxsackieviruses, hepatoviruses, cardioviruses, aptoviruses, echoviruses, hepatitis A virus, Foot and mouth disease virus, and rhinovirus) and Iridoviridae (such as African swine fever virus). Other viruses that can be treated using the methods provided herein include unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (for instance, Hepatitis C); calciviruses (such as Norovirus, Norwalk and related viruses); Hepeviruses (such as Hepatitis E, JC and BK viruses) and astroviruses).

Examples of infectious bacteria that can be treated with the methods provided herein include any type of Gram-positive (such as *Streptococcus, Staphylococcus, Corynebacterium, Listeria, Bacillus* and *Clostridium*) or Gram-negative bacteria (such as *Salmonella, Shigella, Enterobacteriaceae, Pseudomonas, Moraxella, Helicobacter, Stenotrophomonas, Bdellovibrio*, acetic acid bacteria, and alpha-proteobacteria), *Escherichia coli, Neisseria gonorrhoeae, Neisseria meningitidis, Moraxella catarrhalis, Hemophilus influenzae, Klebsiella pneumoniae, Legionella pneumophila, Pseudomonas aeruginosa, Proteus mirabilis, Enterobacter cloacae, Serratia marcescens*). Exemplary infectious bacteria include, but are not limited to: *Helicobacter pyloris, Borelia burgdorferi, Legionella pneumophilia, Mycobacteria* sps (such as *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*.

Examples of infectious fungi that can be treated with the methods provided herein include, but are not limited to, *Cryptococcus neoformans, Histoplasma capsulatum, Coccidioides immitis, Blastomyces dermatitidis, Chlamydia trachomatis*, and *Candida albicans*.

Examples of infectious parasites that can be treated with the methods provided herein include, but are not limited to *Plasmodium falciparum* and *Toxoplasma gondii*.

Pro-inflammatory cytokine. Immunoregulatory cytokines that favor or promote inflammation. Such cytokines are produced predominantly by activated immune cells and are involved in the amplification of inflammatory reactions. Exemplary pro-inflammatory cytokines that are responsible for early responses are IL1-alpha, IL1-beta, IL6, and TNF-alpha. Other pro-inflammatory mediators include LIF, IFN-gamma, OSM, CNTF, TGF-beta, GM-CSF, IL11, IL12, IL17, IL18, IL8 and a variety of other chemokines that chemoattract inflammatory cells. These cytokines can act as endogenous pyrogens (IL1, IL6, TNF-alpha), up-regulate the synthesis of secondary mediators and pro-inflammatory cytokines by both macrophages and mesenchymal cells (including fibroblasts, epithelial and endothelial cells), stimulate the production of acute phase proteins, or attract inflammatory cells.

Retroviruses: RNA viruses wherein the viral genome is RNA. When a host cell is infected with a retrovirus, the genomic RNA in some examples is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV).

Subject: Living multi-cellular vertebrate organisms, a category that includes both human and non-human mammals. The methods and compositions disclosed herein have equal applications in medical and veterinary settings. Therefore, the general term "subject" is understood to include all animals, including, but not limited to, humans or veterinary subjects, such as other primates, dogs, cats, horses, and cows.

TAM receptor: The TAM family (Tyro3, Axl, and Mer) was first identified as a distinct receptor protein-tyrosine kinase (PTK) family (Lai & Lemke, (1991) *Neuron.* 6(5):691-704). Designated Tyro3, Tyro 7, and Tyro 12 at that time, the kinase domains of these proteins clearly segregated into a separate family based on sequence conservation (Lai & Lemke, (1991) *Neuron.* 6(5):691-704). Subsequent isolation of full-length cDNAs by multiple groups confirmed this segregation, and also resulted in multiple names for the receptors. Tyro3, Axl, and Mer are now the consensus, assigned gene designations. An analysis of the mouse and human 'kinomes' indicates that Tyro3, Axl, and Mer constitute the full TAM family. (There are 58 receptor PTK genes in the human and mouse genomes.)

Specific examples of Axl receptor amino acid sequences include, but are not limited to Genbank Accession Nos. NP__001690 (invariant ATP binding Lysine (K) 558) and NP__068713 (as of Jul. 24, 2008). Specific examples of Tyro3 receptor amino acid sequences include, but are not limited to Genbank Accession Nos. NP__006284 (invariant ATP binding Lysine (K) 550), EAW92506, and EAW92507 (as of Jul. 24, 2008). Specific examples of Mer receptor amino acid sequences include, but are not limited to Genbank Accession Nos. AAK54121, AAI14918 (invariant ATP binding Lysine (K) 443), and AAI14918 (as of Jul. 24, 2008). The invariant ATP binding site Lysine (K) is located in the sequence VAVKTM.

"TAM receptor activity" includes any biological activity of a TAM receptor, for instance an activity that is enhanced or induced by the binding of a TAM receptor ligand to a TAM receptor. TAM receptor ligands include Protein S and Gas6. Specific examples of Gas6 nucleic acid and amino acid sequence include, but are not limited to Genbank™ Nos: NM__000820.1 and NP__000811.1 (as of Jul. 24, 2008). Specific examples of Protein S nucleic acid and amino acid sequences include, but are not limited to Genbank™ Nos: Genbank™ Nos: NM__000313.1 and NP__000304.1 (as of Jul. 24, 2008). Exemplary TAM receptor activities include, but are not limited to inhibiting or decreasing IFN-α or IFN-β production in response to infection, inducing TAM autophosphorylation, inhibiting TLR-induced cytokine production, inhibiting TLR-induced stimulation of MAP kinase activation, inhibiting TLR-induced NF-kB activation, and increasing SOCS 1 and/or SOCS3 expression.

An "inhibitor of TAM receptor activity" includes any composition that decreases a TAM receptor activity, for example in a cell that expresses a TAM receptor. Examples of a decrease in TAM receptor activity include, but are not limited to an increase in IFN-α or IFN-β secretion (e.g., by a cell infected with a virus or bacterium), a decrease in TAM autophosphorylation, an increase in TLR-induced cytokine production, an increase in TLR-induced stimulation of MAP kinase activation, an increase in TLR-induced NF-kB activation, and a decrease in SOCS 1 and/or SOCS3 expression. Exemplary methods for measuring such activity are provided herein.

TAM receptor inhibitors include those molecules that reduce TAM receptor activity, such as those that specifically bind to a Tyro3, Axl, or Mer ligand or extracellular domain and prevent the interaction between the ligand and the receptor, molecules that decrease TAM receptor ligand concentration (such as decreasing Protein S and or Gas6 levels using Protein S or Gas6 specific siRNA or antibodies), and molecules that bind to the intracellular domain (e.g., a kinase domain or ATP binding site) and prevent signaling of the receptor (and thus significantly reduce or inhibit receptor activation). Exemplary inhibitors include the small molecule inhibitors of TAM (e.g., Axl) kinase activity, as well as antibodies that (a) bind to TAM receptors and block receptor activation, (b) block the interaction of TAM receptors with Gas6 or ProS ligands, or (c) bind to the ligands and prevent them from activating their cognate TAM receptors, and RNAi molecules that significantly decrease or inhibit expression of Tyro3, Axl or Mer. Several TAM receptor inhibitors are known, for instance AXL-1, AXL-2, AXL-3, AXL-4, AXL-5, AXL-6, AXL-7, AXL-8, AXL-9, MP470, and SGI-AXL-277. Other small molecule TAM receptor inhibitors are described in this application.

Therapeutically effective amount: An amount of a therapeutic agent (such as a TAM receptor inhibitor), alone or in combination with other agents (such as an anti-infective agent) sufficient to prevent advancement of a disease, to cause regression of the disease, or which is capable of relieving symptoms caused by the disease, such as fever, respiratory symptoms, pain or swelling. In some examples, it is an amount that results in a decrease of symptoms upon pathogen infection or results in a delay, amelioration, or prevention of a disease associated with infection by a pathogen. The particular dose for a therapeutically effective amount of a particular TAM receptor inhibitor will depend on the particular inhibitor used, the weight, age and condition of the subject to be treated, the drug combination used, and the like. However, such amounts can be determined using methods well known in the art. In a particular example, a therapeutically effective amount of a TAM receptor inhibitor is 0.001 mg/kg to 100 mg/kg for a 70 kg mammal, such as 0.01 to 50 mg/kg, or 1 to 25 mg/kg. In another particular example, a therapeutically effective amount of a TAM receptor inhibitor is 0.001 μg/kg to 100 μg/kg for a 70 kg mammal, such as 0.01 to 50 μg/kg, or 1 to 25 μg/kg.

Treating a disease: "Treatment" refers to a therapeutic intervention that ameliorates a sign or symptom of a disease or pathological condition (e.g., a bacterial or viral infection) after it has begun to develop. As used herein, the term "treatment" also encompasses "prevention," which refers to inhibiting the full development of a disease, for example in a person who is known to have a predisposition to a disease such as a person who has been or is at risk for being exposed to a pathogen. Examples of persons at risk for being exposed to an infective agent include, but are not limited to, military personnel, medical personnel, travelers, and caregivers of adults and children, as well as those with weakened immune systems, for example, the elderly, people on immunosuppressive drugs, subjects with cancer, and subjects infected with HIV.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8). All GenBank Numbers referenced herein are incorporated by reference (that is, the sequence associated with each GenBank number on Jul. 24, 2008 is incorporated by reference).

The singular terms "a," "an," and "the" include plural referents unless context clearly indicates otherwise. "Comprising" means "including." "Comprising A or B" means "including A," "including B," or "including A and B." It is further to be understood that all base sizes or amino acid sizes and all molecular weight or molecular mass values given for nucleic acids or peptides are approximate, and are provided for description.

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification (see, for instance, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999).

IV. Use of TAM Receptor Inhibitors as Antimicrobials

A. Overview

The novel use of TAM receptor inhibitors as antimicrobial agents (e.g., anti-viral and anti-bacterial) is described herein. In some examples, inhibition of the TAM pathway during a viral or other pathogen infection causes reduction in infection. Without wishing to be bound to a particular theory, it is proposed that this is due to the potentiation of type I interferon (IFN) production, resulting in an increased antimicrobial response and consequent clearance of the infectious agent. In contrast, presence of a functional TAM pathway during a viral or other pathogen infection results in higher infectivity which could be due to the significant reduction or inhibition of type I IFN production, resulting in a decreased immune response and consequently less or no clearance of the infectious agent. These results provided herein are consistent with longstanding observations that early induction of a type I IFN response is essential for the control of viral infection. The results also indicate that inhibitors of TAM receptor signaling (e.g., membrane permeable small molecules that specifically bind to the intracellular kinase domain as well as agents that interfere with ligand binding to the receptor or activation of the receptor) might serve as potent, short-acting antimicrobial (e.g., anti-viral and anti-bacteria) therapies.

For example, methods are provided to increase production of pro-inflammatory cytokines (e.g., type I IFN) in a subject who has been infected with a pathogen, thereby increasing the subject's immune response to the pathogen. In one example, administration of one or more TAM receptor inhibitors to a mammal increases production of type I IFN cytokines (e.g., IFNα or IFN-β) by the mammal by at least 20%, at least 50%, at least 75%, at least 85% at least 95%, at least 100%, at least 200%, or even at least 500%, for example as compared to such a response in the absence of the inhibitor. This approach targets a previously unknown or unappreciated signaling pathway, as previous efforts have been based on the direct stimulation of inflammation (i.e., TLR agonists), which is invariably compensated by negative feedback mechanisms, such as the TAM pathway (Rothlin et al., *Cell* 131:1124-36, 2007; Lemke and Rothlin, *Nature Rev. Immunol.* 8:327-36, 2008).

As schematized in FIG. 1, TAM-mediated suppression of type I IFN production in fact requires the formation of a physical and functional interaction with the type I IFN receptor (IFNAR in FIG. 1). That is, that suppression of IFN production paradoxically requires IFN itself. Given that mice that lack the type I IFN receptor are resistant to persistent infection with certain gram-negative bacteria (e.g., *Listeria monocytogenes*; see O'Connell et al., *J. Exp. Med.* 200:437-45, 2004), TAM receptor inhibitors may also be effective in combating these and other bacterial infections. Without wishing to be bound to a particular theory, continued TAM activation is immunosuppressive in the face of these chronic infections. In particular examples, TAM receptor inhibitors will specifically perturb only the later-acting immunosuppressive activities of type I IFNs, and not their earlier-acting pro-inflammatory activities, which are required for the immediate response to viral and bacterial infections. That is, in some examples the disclosed methods do not prevent pathogen entry into a cell.

Stages of viral infection of a host cell include viral entry, fusion, uncoating, reverse transcription (e.g., for Retroviruses and hepadnaviruses), integration, transcription and translation, and assembly and budding. Viral entry includes attachment of the virus to the target cell via a specific interaction between a virus envelope glycoprotein and a receptor on the cell surface, co-receptor binding (which can include conformational changes in the cell surface receptor leading to exposure of the co-receptor binding site), and fusion where the membranes of virus and host-cell are brought into close apposition, an opening called a fusion pore is created and viral RNA is released from the retroviral core into the target cell's cytoplasm. After fusion of the viral and cellular membranes, the viral capsid enters the cell. In some examples, if the virus is an RNA virus, reverse transcriptase transcribes single-stranded RNA into double-stranded DNA. The resulting DNA (or the DNA of a DNA virus) is then integrated into the host cell chromosome (e.g., by the viral enzyme integrase). Host cellular enzymes transcribe the provirus into mRNA molecules that encode viral regulatory and structural genes. The last stages of viral replication involve both the assembly of the viral particles and the budding and release of the virus from the cell surface. In particular examples, a TAM receptor inhibitor targets one or more of the following stages of viral infection: reverse transcription, integration, transcription and translation, and assembly and budding. In one example, the methods provided herein do not target viral entry.

Stages of bacterial infection can include adherence, entry into host cells and tissues, and replication. During adherence, the bacterium attaches to the host cell. In some examples, bacterial adhesion to host tissues is produced by individual proteins (e.g., bacterial cell wall/membrane adhesins or ligands that bind specifically to host cell surface receptors) or by organelles such as fimbriae and pili. Bacteria can also secrete viscous substances onto their surface (e.g., alginate capsule and polysaccharide slime) which increase adherence to host cells in a non-specific fashion. After adhering to the cell surface, bacteria enter the cell, for example via endocytosis or phagocytosis. Bacterial entry into cells may lead to an infection that is limited to that cell type, or it may be a first step towards wider dissemination of the infecting agent throughout the body. Some bacteria secrete toxins into the extracellular milieu during infection. Such toxins can damage host cell membranes, thus allowing the bacterium to enter the cell. The bacterial infection may or may not result in death of the cell. In particular examples, a TAM receptor inhibitor can target the replication stage of bacterial infection, but not bacterial entry.

B. TAM Receptor Inhibitors

TAM receptors are receptor tyrosine kinases. These cell surface receptor proteins include an extracellular ligand-binding domain (e.g., a domain that binds Gas6 or Protein S), a transmembrane spanning domain, and an intracellular domain responsible for kinase activity. In some examples, TAM receptor inhibitors target the extracellular domain. Thus, such inhibitors can include antibodies (e.g., monoclonal antibodies, for example humanized monoclonal antibodies) or other small molecules that bind to a Tyro3, Axl, or Mer ligand, or a Tyro3, Axl, or Mer receptor, and prevent or significantly reduce the interaction of the ligand binding to the receptor. In one examples, a TAM receptor inhibitor is an agent that reduces the TAM receptor ligand concentration, for example by using Protein S or Gas6 specific siRNA or antibodies that reduce Protein S or Gas6 nucleic acid or protein levels in the cell (or reduces the biological activity of such proteins present). In another example, such inhibitors target a Tyro3, Axl, or Mer intracellular domain, such as a kinase domain, and thus prevent signaling from the receptor and reduce or inhibit downstream biological effects. Thus, such inhibitors can include small molecule inhibitors, for example those that are membrane permeable.

The TAM receptors share an arrangement of sequence motifs in their extracellular regions in which two tandem immunoglobulin (Ig)-related domains are immediately followed by two fibronectin type III (FNIII)-related repeats. These receptors are the only receptor PTKs to display this particular array of Ig and FNIII domains. The ectodomains of Tyro3, Axl, and Mer are all followed closely by a single transmembrane domain, a relatively large cytoplasmic juxtamembrane region, and a split tyrosine kinase domain. Specific examples of Axl receptor amino acid sequences include, but are not limited to Genbank Accession Nos. NP_001690 and NP_068713 (as of Jul. 24, 2008). Specific examples of Tyro3 receptor amino acid sequences include, but are not limited to Genbank Accession Nos. NP_006284, EAW92506, and EAW92507 (as of Jul. 24, 2008). Specific examples of Mer receptor amino acid sequences include, but are not limited to Genbank Accession Nos. AAK54121, AAI14918, and AAI14918 (as of Jul. 24, 2008). For example, the extracellular domain of human Axl (NP_068713.2) spans amino acid positions from about position 1 to about position 445 amino and contains two Ig domains and two FNIII domains. The first Ig domain, denoted herein as IgI, includes from about position 33 to about position 137. The second Ig domain, denoted herein as Ig2, includes from about position 139 to about position 222 of SEQ ID NO:2. The first FNIII domain, denoted herein as FNIII(a), includes from about position 225 to about position 328. The second FNIII domain, denoted herein as FNIII(b), includes from about position 337 to about position 418. Further, the intracellular domain, such as the intracellular domain of Mer (such as the amino acid sequence of Mer Genbank Accession No. NP_032613.1 as of Nov. 7, 2008) spans amino acid positions from about position 521 to about position 994.

The positions of each of the domains of each of the TAM receptors, including their ligand binding domains and the ATP and substrate binding sites of the protein-tyrosine kinase domains, are known and are readily accessible in public NCBI and National Library of Medicine (NLM) databases. For example, the extracellular domain of the human Tyro3 protein (GenBank Accession No. EAW92508 as of Nov. 7, 2008), includes a first Ig domain from about position 41 to about position 120, a second Ig domain from about position 130 to about position 205, a first FNIII domain from about position 215 to about position 305, and a second FNIII domain from about position 315 to about position 397. The Tyro3 protein-tyrosine kinase domain extends from about position 510 to about position 730. The extracellular domain of the human c-Mer protein (GenBank Accession No. EAW52097 as of Nov. 7, 2008) contains a first Ig domain from about position 115 to about position 187, a second Ig domain from about position 195 to about position 280, a first FNIII domain from about position 285 to about position 375, and a second FNIII domain from about position 387 to about position 478. The c-Mer substrate binding site extends from about position 725 to about position 750.

The TAM receptor ligands include Protein S and Gas6. Protein S (ProS) is an anticoagulant in the blood coagulation cascade. It acts as a co-factor for activated protein C, a protease that degrades Factor V and Factor VIII and thereby inhibits blood coagulation. Gas6, an acronym for growth-arrest-specific protein 6, was originally identified in a screen for mRNAs that were induced when fibroblasts were growth arrested in culture. Gas6 is expressed in discrete cellular loci in a variety of adult tissues, very often in cell layers that are apposed to or intermingled with cells that express Tyro3, Axl, or Mer (Lu & Lemke, (2001) *Science.* 293(5528):306-11). Many cell types co-express both Gas6 and Protein S, and at the same time also express one or more TAM receptors (Lu & Lemke, (2001) *Science.* 293(5528):306-11).

Gas6 and Protein S exhibit 44% amino acid sequence identity overall, share the same complex multi-domain structure, and are the only two proteins encoded in the mouse and human genomes that display this configuration of domains. The amino-terminal segments of both proteins contain long strings of glutamic acids residues that are carboxylated on their γ carbons, in a vitamin K-dependent reaction in the Golgi. These so called 'Gla-domains', whose γ carboxylation is essential to both $Ca^{+2}$ binding and full biological activity, are common to a number of proteins that bind polar phospholipids such as phosphatidylserine (PS). The extracellularly-displayed PS is a signature of apoptotic cells. In Gas6 and ProS, the Gla domain (such as amino acids 49-90 of Gas6) is closely followed by a loop domain (amino acids 91-117 of Gas6), and then by four tandem EGF-related domains (amino acids 118-278 of Gas6). These are in turn followed by a carboxy-terminal domain that contains two laminin G repeats (amino acids 279-678 of Gas6) that are structurally related to those of the sex hormone binding globulin (SHBG). The SHBG-related domains of Gas6 and ProS account for both ligand binding and receptor activation, and will fully activate the TAM receptors in the absence of the Gla domain.

TAM receptor inhibitors include agents that significantly reduce or even inhibit the biological activity of a TAM receptor in a cell. Such agents need not inhibit TAM receptor activity by 100%, lesser amounts can be effective in the methods provided herein. For example, a TAM receptor inhibitor may decrease the biological activity by at least 25%, at least 50%, at least 70%, at least 80%, at least 90%, at least 95%, or even at least 99%. Methods of measuring such activity are known in the art. In some examples, a decrease in biological activity is indicated by a decrease in expression of Tyro3, Axl, or Mer or combinations thereof (at the DNA, RNA, or protein level). In other examples, a decrease in biological activity is indicated by a decrease in a downstream effect, such as viral nucleic acid replication. In yet other examples, a decrease in biological activity is indicated by an increase in a downstream effect, such as an increase in Type I IFN (e.g., IFNα or IFN-β) and/or IRF (e.g., IRF3, IRF5, IRF7, etc.) production or mRNA levels in the presence of pathogen. Methods of detecting such alternations in expression or activity (which in some examples are quantified) are routine, and can include western blotting, ELISA, flow cytometry, northern blotting, PCR, RT-PCR, and the like.

In some embodiments, a TAM receptor inhibitor has an $IC_{50}$ of less than about 50 μM, for instance, less than about 50 nM, such as 0.1 nM to 20 nM, or 0.1 pM to 50 pM, and in particular embodiments, a TAM receptor inhibitor has an $IC_{50}$ of less than from about 0.005 nM to about 50 nM or from about 0.05 nM to about 50 nM. In addition to the known TAM receptor inhibitors, higher potency inhibitors are generated by chemical modification of the existing inhibitors. For instance, the known compounds generally work in the low micromolar or low nanomolar range, however chemical modification makes them, in some embodiments, more potent and more specific (e.g., work in the low picomoloar range). In one embodiment, QSAR analysis is performed using the solved Kinase Domain Crystal Structure of MERTK. Axl and Tyro3 kinases also may be modeled upon this crystal structure (see, for instance, Walker, Huang, Finerty Jr., Weigelt, Sundstrom, Arrowsmith, Edwards, Bochkarev, Dhe-Paganon, Human Proto-oncogene Tyrosine-protein Kinase MER; PDB (protein data base) 2P0C). These more potent compositions will have lower $IC_{50}$ values.

In some examples, a TAM receptor inhibitor specifically binds to a target (such as a extracellular binding domain, ligand, or intracellular kinase domain of Tyro, Axl, or Mer) with a binding constant that is at least $10^3$ $M^{-1}$ greater, $10^4$ $M^{-1}$ greater or $10^5$ $M^{-1}$ greater than a binding constant for other molecules in a sample. In some examples, a TAM receptor inhibitor (such as an aptamer, antibody (e.g., monoclonal antibody) or fragments thereof) has an equilibrium constant ($K_d$) of 1 nM or less. For example, TAM receptor inhibitors are provided that bind to a TAM receptor (such as a extracellular binding domain, ligand, or intracellular kinase domain of Tyro, Axl, or Mer) with a binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M. Kd values can, for example, be determined by competitive ELISA (enzyme-linked immunosorbent assay) or using a surface-plasmon resonance device such as the Biacore T100, which is available from Biacore, Inc., Piscataway, N.J.

The ability of a TAM receptor inhibitor (e.g., RNAi, aptamer, antibody, or membrane permeable small molecule) to function as an antimicrobial can be performed using the methods described in Section IV, E below. For example, potential TAM receptor inhibitors can be screened for their ability to function as an antimicrobial (e.g., anti-viral or anti-bacterial agent). In some examples, the ability of potential TAM receptor inhibitors to decrease viral or bacterial replication is tested. For example, nucleic acid replication can be measured using qPCR such as qRT-PCR. In other examples, the ability of potential TAM receptor inhibitors to increase type I IFN (e.g., IFNα or IFN-β) or IRF production is determined (for example by measuring protein expression using ELISA).

1. Membrane-permeable Small Molecules

In some embodiments, TAM receptor inhibitors are small molecule inhibitors that bind to an ATP binding site of Tyro3, Axl, or Mer. Specific examples of Axl receptor amino acid sequences include, but are not limited to Genbank Accession Nos. NP_001690 (invariant ATP binding Lysine (K) 558) and NP_068713 (as of Sep. 5, 2007). Specific examples of Tyro 3 receptor amino acid sequences include, but are not limited to Genbank Accession Nos. NP_006284 (invariant ATP binding Lysine (K) 550), EAW92506, and EAW92507 (as of Sep. 5, 2007). Specific examples of Mer receptor amino acid sequences include, but are not limited to Genbank Accession Nos. AAK54121, AAI14918 (invariant ATP binding Lysine (K) 443), and AAI14918 (as of Sep. 5, 2007). The invariant ATP binding site Lysine (K) is located in the sequence VAVKTM.

In some examples, small molecule inhibitors that bind to an intracellular kinase domain of Tyro3, Axl, or Mer, can be used to decrease the biological activity of a TAM receptor in a cell. In particular examples, the small molecule inhibitor is membrane permeable. In some examples, a TAM receptor inhibitor is a triazole compound or derivative thereof, such as an inhibitor of Axl catalytic activity (particular examples can be found in US Patent Publication Nos. 20070213375 and 20080153815, both herein incorporated by reference). Several small molecule TAM receptor inhibitors are known, for instance AXL-1, AXL-2, AXL-3, AXL-4, AXL-5, AXL-6, AXL-7, AXL-8, AXL-9, MP470, and SGI-AXL-277. Other small molecule TAM receptor inhibitors can be obtained, for example, from Rigel Pharmaceuticals, Inc., San Francisco, Calif. and SuperGen, Inc., Dublin, Calif. Other specific examples of TAM receptor inhibitors can be found in PCT Publication Nos: WO07030680A3, WO06052936A3, WO04092735A3, WO07056151A2, and U.S. Patent Publication No: US20070142402 (all hereby incorporated by reference). In some examples, the AXL inhibitor is a triazole derivative. Examples of AXL inhibitors are disclosed in U.S. Patent Publication 2007/0213375, filed Sep. 13, 2007, which is incorporated herein by reference in its entirety. In certain examples, the AXL inhibitor is a triazole derivative with one of the following general structures:

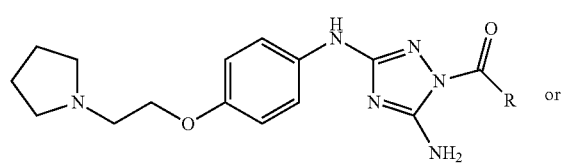

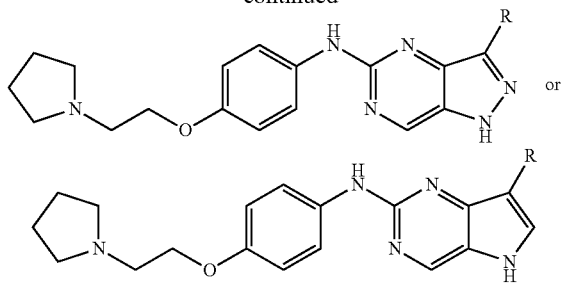

wherein R can be H or CH$_3$.

In addition to the known TAM receptor inhibitors, higher potency inhibitors are generated by chemical modification of the existing inhibitors. For instance, the known compounds generally work in the low micromolar range, however chemical modification makes them, in some embodiments, more potent and more specific. In one embodiment, QSAR analysis is performed using the solved Kinase Domain Crystal Structure of MERTK. Axl and Tyro3 kinases also may be modeled upon this crystal structure (see, for instance, Walker, Huang, Finerty Jr., Weigelt, Sundstrom, Arrowsmith, Edwards, Bochkarev, Dhe-Paganon, Human Proto-oncogene Tyrosine-protein Kinase MER (in press); PDB (protein data base) 2P0C). These more potent compositions will have lower IC$_{50}$ values.

2. Antibodies

In some embodiments, a TAM receptor inhibitor is an anti-Mer, anti-Tyro3, or anti-Axl antibody, for instance, an anti-human Mer, Tyro3, or Axl monoclonal or polyclonal antibody. Examples of anti-TAM receptor antibodies can be found in, for example, Varnum et al., (1995) *Nature*, 373:623-626 and Gallicchio et al., (2005) *Blood*, 105:1970-1976. The antibodies encompassed by the present disclosure include any antibody that selectively binds to a conserved binding surface or epitope of a Tyro3, Axl, or Mer protein, for instance, a conserved binding surface or epitope in the extracellular domain of a Tyro3, Axl, or Mer protein, or an antibody that is able to bind a TAM receptor ligand (e.g., Gas6 or Protein S), and impair the interaction between the ligand and the TAM receptor or decrease available ligand available to bind to the receptor. An "epitope" of a given protein or peptide or other molecule is a part of or a site on a larger molecule to which an antibody or antigen-binding fragment thereof will bind, and against which an antibody will be produced. An epitope can be defined by both the amino acid residues involved in antibody binding and also by their conformation in three dimensional space (for instance, a conformational epitope or the conserved binding surface). An epitope can be included in peptides as small as about 4-6 amino acid residues, or can be included in larger segments of a protein (e.g., 7-12 amino acids), and need not be comprised of contiguous amino acid residues when referring to a three dimensional structure of an epitope, particularly with regard to an antibody-binding epitope. For example, an epitope of an extracellular domain of a TAM receptor or a TAM ligand can be used to generate antibodies useful for the disclosed methods. Antibody-binding epitopes are frequently conformational epitopes rather than sequential epitopes, or in other words, an epitope defined by amino acid residues arrayed in three dimensions on the surface of a protein or polypeptide to which an antibody binds.

Disclosed TAM receptor inhibitors include antibodies. The term "antibody" refers to an immunoglobulin molecule (or combinations thereof) that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), single chain Fv antibodies (scFv), polypeptides that contain at least a portion of an immunoglobulin that is sufficient to confer specific antigen binding to the polypeptide, and antigen binding fragments of antibodies. Antibody fragments include proteolytic antibody fragments [such as F(ab')2 fragments, Fab' fragments, Fab'-SH fragments, Fab fragments, Fv, and rIgG], recombinant antibody fragments (such as sFv fragments, dsFv fragments, bispecific sFv fragments, bispecific dsFv fragments, diabodies, and triabodies), complementarity determining region (CDR) fragments, camelid antibodies (see, for example, U.S. Pat. Nos. 6,015,695; 6,005,079; 5,874,541; 5,840,526; 5,800,988; and 5,759,808), and antibodies produced by cartilaginous and bony fishes and isolated binding domains thereof (see, for example, International Patent Application No. WO03014161).

A Fab fragment is a monovalent fragment consisting of the VL, VH, CL and CH1 domains; a F(ab')$_2$ fragment is a bivalent fragment comprising two Fab fragments linked by a disulfide bridge at the hinge region; an Fd fragment consists of the VH and CH1 domains; an Fv fragment consists of the VL and VH domains of a single arm of an antibody; and a dAb fragment consists of a VH domain (see, e.g., Ward et al., *Nature* 341:544-546, 1989). A single-chain antibody (scFv) is an antibody in which a VL and VH region are paired to form a monovalent molecule via a synthetic linker that enables them to be made as a single protein chain (see, e.g., Bird et al., *Science*, 242: 423-426, 1988; Huston et al., *Proc. Natl. Acad. Sci. USA*, 85:5879-5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al., *Proc. Natl. Acad. Sci. USA*, 90:6444-6448, 1993; Poljak et al., *Structure*, 2:1121-1123, 1994). A chimeric antibody is an antibody that contains one or more regions from one antibody and one or more regions from one or more other antibodies. An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a "bispecific" or "bifunctional" antibody has two different binding sites.

As used herein, the term "selectively binds to" refers to the specific binding of one protein to another (for instance, an antibody, fragment thereof, or binding partner to an antigen), wherein the level of binding, as measured by any standard assay (for example, an immunoassay), is statistically significantly higher than the background control for the assay. For example, when performing an immunoassay, controls typically include a reaction well/tube that contain antibody or antigen binding fragment alone (for instance, in the absence of antigen), wherein an amount of reactivity (for instance, non-specific binding to the well) by the antibody or antigen binding fragment thereof in the absence of the antigen is considered to be background.

In some examples, an antibody specifically binds to the extracellular domain of a TAM receptor (e.g., Tyro3, Axl, or Mer) or ligand thereof (e.g., Gas6 or Protein S) with a binding constant that is at least $10^3 M^{-1}$ greater, $10^4 M^{-1}$ greater or $10^5 M^{-1}$ greater than a binding constant for other molecules in a sample. In some examples, such antibodies (e.g., monoclonal antibody) or fragments thereof has an equilibrium constant ($K_d$) of 1 nM or less. For example, antibodies that bind to a TAM receptor or ligand thereof with a binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M. Kd values can, for example, be determined by competitive ELISA (enzyme-linked immunosorbent assay) or using a surface-plasmon resonance device such as the Biacore T100, which is available from Biacore, Inc., Piscataway, N.J.

Binding can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorptional ionization time-of-flight mass spectrometry, microcytometry, microarray, microscopy, fluorescence activated cell sorting (FACS), and flow cytometry.

In some embodiments, an anti-TAM receptor antibody or antigen binding fragment thereof is a competitive inhibitor of the binding of a Tyro3, Axl, or Mer ligand (for instance, Gas6 or Protein S). A competitive inhibitor is an inhibitor (for instance, a small molecule inhibitor, antibody, or antigen binding fragment or polypeptide) that binds to Tyro3, Axl, or Mer that is expressed by a cell, and that significantly reduces or inhibits the binding of a Tyro3, Axl, or Mer ligand (for instance, Gas6 or Protein S) to the Tyro3, Axl, or Mer that is expressed by the cell. A competitive inhibitor can bind to the target with a greater affinity for the target than the Tyro3, Axl, or Mer ligand. Competition assays can be performed using standard techniques in the art (for instance, competitive ELISA or other binding assays). For example, competitive inhibitors can be detected and quantified by their ability to inhibit the binding of Tyro3, Axl, or Mer to another, labeled anti-Tyro3, Axl, or Mer antibody or ligand.

Isolated antibodies can include serum containing such antibodies, or antibodies that have been purified to varying degrees. Whole antibodies can be polyclonal or monoclonal. Alternatively, functional equivalents of whole antibodies, such as antigen binding fragments in which one or more antibody domains are truncated or absent (for instance, Fv, Fab, Fab', or F(ab)2 fragments), as well as genetically-engineered antibodies or antigen binding fragments thereof, including single chain antibodies, humanized antibodies, antibodies that can bind to more than one epitope (for instance, bi-specific antibodies), or antibodies that can bind to one or more different antigens (for instance, bi- or multi-specific antibodies), also can be used.

In one embodiment, an anti-Tyro3, Axl, or Mer antibody (or antibody specific for a ligand thereof) is a humanized antibody. Humanized antibodies are molecules having an antigen binding site derived from an immunoglobulin from a non-human species, the remaining immunoglobulin-derived parts of the molecule being derived from a human immunoglobulin. The antigen binding site can include either complete variable regions fused onto human constant domains or only the complementarity determining regions (CDR5) grafted onto appropriate human framework regions in the variable domains. Humanized antibodies can be produced, for example, by modeling the antibody variable domains, and producing the antibodies using genetic engineering techniques, such as CDR grafting. A description of various techniques for the production of humanized antibodies can be found, for example, in Morrison et al. (1984) *Proc. Natl. Acad. Sci. USA* 81:6851-6855; Whittle et al. (1987) *Prot. Eng.* 1:499-505; Co et al. (1990) *J. Immunol.* 148:1149-1154; Co et al. (1992) *Proc. Natl. Acad. Sci. USA* 88:2869-2873; Carter et al. (1992) *Proc. Natl. Acad. Sci.* 89:4285-4289; Routledge et al. (1991) *Eur. J. Immunol.* 21:2717-2725 and PCT Patent Publication Nos. WO 91/09967; WO 91/09968 and WO 92/113831.

Other embodiments include fully human antibodies. One method to produce such antibodies having a particular binding specificity includes obtaining human antibodies from immune donors (for instance, using EBV transformation of B-cells or by PCR cloning and phage display). In addition, and more typically, synthetic phage libraries have been created that use randomized combinations of synthetic human antibody V-regions. By selection on the antigen, fully human antibodies can be made in which the V-regions are very human-like in nature. Finally, fully human antibodies can be produced from transgenic mice. Specifically, transgenic mice have been created which have a repertoire of human immunoglobulin germline gene segments. Therefore, when immunized, these mice produce human-like antibodies. All of these methods are known in the art.

Genetically engineered antibodies include those produced by standard recombinant DNA techniques involving the manipulation and re-expression of DNA encoding antibody variable and/or constant regions. Particular examples include, chimeric antibodies, where the VH and/or VL domains of the antibody come from a different source as compared to the remainder of the antibody, and CDR grafted antibodies (and antigen binding fragments thereof), in which at least one CDR sequence and optionally at least one variable region framework amino acid is derived from one source, and the remaining portions of the variable and the constant regions (as appropriate) are derived from a different source. Construction of chimeric and CDR-grafted antibodies is described, for example, in European Patent Applications EP-A 0194276, EP-A 0239400, EP-A 0451216 and BP-A0460617. In one embodiment, chimeric antibodies are produced that include antibody variable domains that bind to Tyro3, Axl, or Mer (or ligand thereof), and fused to these domains is a protein that serves as a second targeting moiety. For example, the targeting moiety can include a protein that is associated with the cell or tissue to be targeted or with a particular system in the animal.

Methods of generating antibodies (such as monoclonal or polyclonal antibodies) are well established in the art (for example, see Harlow and Lane, *Antibodies: A Laboratory Manual*, Cold Spring Harbor Laboratory, New York, 1988). Generally, in the production of a polyclonal antibody, a suitable experimental animal, such as, for example, a rabbit, a sheep, a hamster, a guinea pig, a mouse, a rat, or a chicken, is exposed to an antigen against which an antibody is desired (e.g., against an extracellular TAM receptor domain or ligand thereof). Typically, an animal is immunized with an effective amount of antigen that is injected into the animal. An effective amount of antigen refers to an amount needed to induce antibody production by the animal. In some examples, the antigen is administered with an adjuvant. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies can be produced according to the methodology of Kohler & Milstein (*Nature* 256:495-497, 1975), or using the human B-cell hybridoma method (Kozbor (1984) *Immunol*, 133:3001; Brodeur et al., *Monoclonal Antibody Production Techniques and Applications*, pp. 51-63 (Marcel Dekker, Inc., New York, 1987). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen. The hybridomas can be cloned and the antibodies can be produced by and then isolated from the hybridomas. An exemplary method for producing a monoclonal anti-TAM receptor antibody includes (a) administering to an animal an effective amount of a protein or peptide (for instance, a Tyro3, Axl, or Mer ligand (for instance, Gas6 or Protein S) or a Tyro3, Axl, or Mer peptide, such as a Tyro3, Axl, or Mer extracellular domain or immunogenic portion thereof) to produce the antibodies, and (b) recovering the antibodies. As used herein, the term "monoclonal antibody" includes chimeric, humanized, and human forms of a monoclonal antibody. Monoclonal antibodies often are synthesized in the laboratory in pure form by a single clone (population) of cells. These antibodies can be made in large quantities and have a specific affinity for certain target antigens which can be found on the surface of cells.

In one example, monoclonal antibody to a TAM receptor (e.g., an epitope of the extracellular domain) or TAM receptor ligand (or epitope of the ligand) can be prepared from murine hybridomas according to the classical method of Kohler and Milstein (*Nature*, 256:495, 1975) or derivative methods thereof. In one exemplary method, a mouse (such as Balb/c 6-8 weeks old) are immunized is repetitively inoculated (e.g., 3-6 times) with a few micrograms of the selected peptide or carrier conjugate thereof over a period of a few weeks. In some examples, mice can be injected three times intradermally into the base of the tail on days 0, 10, and 20 using an insulin syringe with a 28-gauge needle attached. Serum can be drawn on days 30 and 45 for evaluation of the anti-serum titer. The mouse is then sacrificed, and the antibody-producing cells of the spleen isolated. Spleens can be harvested about 80-90 hours after the last cell boost for cell fusion. The spleen cells are fused by means of polyethylene glycol with mouse myeloma cells, and the excess unfused cells destroyed by growth of the system on selective media comprising aminopterin (HAT media). For example, cell fusions of the splenocytes can be performed according to the protocol of Oi and Herzenberg (*Selected Methods in Cellular Immunology*, Freeman Press, San Francisco, 1980). Splenocytes and SP2/0 cells are mixed, for example at a 4:1 ratio. The mixed cells are centrifuged and the cell pellet resuspended in polyethylene glycol (such as 40%-50% (w/v) polyethylene glycol) and appropriate medium. The resulting suspension is centrifuged and the cell pellet resuspended in HAT medium, and seeded in 96-well plates at 100 µl/well ($2.5 \times 10^5$ cells/well) and cultured in a $CO_2$ incubator. On the day after fusion, 100 µl of fresh HAT medium containing 500 µg/ml geneticin (Invitrogen) is added. On days 4 and 7, half of the spent medium is replaced by fresh HAT medium containing 250 µg/ml geneticin. On day 8, the growth of the hybridoma in each well is checked under a microscope. The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.*, 70:419, 1980), and derivative methods thereof. For example, mAb production in culture supernatants can be assayed on day 10 by ELISA assay or days 9 and 10 by FACS sorter. Positive clones can be expanded and the specific hybridomas cloned by a limiting dilution method. Selected positive clones can be expanded and their monoclonal antibody product harvested for use.

In another example, an anti-Tyro3, Axl, or Mer (or ligand thereof) monoclonal antibody is produced recombinantly. For example, once a cell line expressing an antibody, for example a hybridoma, has been obtained, it is possible to clone therefrom the cDNA and to identify the variable region genes encoding the desired antibody, including the sequences encoding the CDRs. Then, antibodies and antigen binding fragments can be obtained by preparing one or more replicable expression vectors containing at least the DNA sequence encoding the variable domain of the antibody heavy or light chain and optionally other DNA sequences encoding remaining portions of the heavy and/or light chains as desired, and transforming/transfecting an appropriate host cell, in which production of the antibody will occur. Suitable expression hosts include bacteria, (for example, an *E. coli* strain), fungi, (in particular yeasts (for instance, members of the genera *Pichia, Saccharomyces*, or *Kluyveromyces*), and mammalian cell lines, (for example, a non-producing myeloma cell line, such as a mouse NSO line, or CHO cells). In order to obtain efficient transcription and translation, the DNA sequence in each vector includes appropriate regulatory sequences, particularly a promoter and leader sequence operably linked to the variable domain sequence. Particular methods for producing antibodies in this way are known and routinely used. For example, basic molecular biology procedures are described by Maniatis et al. (*Molecular Cloning*, Cold Spring Harbor Laboratory, New York, 1989); DNA sequencing can be performed as described in Sanger et al. (PNAS 74:5463, (1977)) and the Amersham International plc sequencing handbook; and site directed mutagenesis can be carried out according to the method of Kramer et al. (*Nucl. Acids Res.* 1:9441, (1984)) and the Anglian Biotechnology Ltd. handbook. Additionally, there are numerous publications, including patent specifications, detailing techniques suitable for the preparation of antibodies by manipulation of DNA, creation of expression vectors and transformation of appropriate cells, for example, as reviewed by Mountain & Adair in *Biotechnology and Genetic Engineering Reviews* (ed. Tombs, M P, 10, Chapter 1, 1992, Intercept, Andover, UK).

In another example, monoclonal antibody to a TAM receptor (e.g., an epitope of the extracellular domain) or TAM receptor ligand can be prepared from rabbit hybridomas as described in U.S. Pat. Nos. 7,148,332, 5,675,063, or 4,859, 595.

In yet another example, monoclonal antibodies to a TAM receptor (e.g., an epitope of the extracellular domain) or TAM receptor ligand can be prepared by repetitively inoculating a non-human mammal (such as a mouse or rabbit) with one or more plasmids encoding a TAM receptor (e.g., an epitope of the extracellular domain) or TAM receptor ligand (or fragment thereof). For example, pcDNA3 (Invitrogen, Carlsbad, Calif.) or a vector derived there from, can be manipulated using standard molecular biology methods to include a coding sequence for a peptide fragment of a TAM receptor (e.g., an epitope of the extracellular domain) or TAM receptor ligand. In one exemplary method, Balb/c mice (6-8 weeks old) are immunized three times with the appropriate plasmid (20 µg in phosphate-buffered saline), and one boost can be given with cells before fusion. Mice can be injected three times intradermally into the base of the tail on days 0, 10, and 20 using an insulin syringe with a 28-gauge needle attached. Serum can be drawn on days 30 and 45 for evaluation of the anti-serum titer. To boost the immunized mice, cells expressing the desired plasmid are injected (for example on day at least 50). These injections can be intravenous and intraperitoneal. Spleens are harvested about 80-90 hours after the last cell boost for cell fusion. Cell fusions of the splenocytes can be performed according to the protocol of Oi and Herzenberg (*Selected Methods in Cellular Immunology*, Freeman Press, San Francisco, 1980). Splenocytes and SP2/0 cells are mixed, for example at a 4:1 ratio. The mixed cells are centrifuged and the cell pellet resuspended in polyethylene glycol (such as 40%-50% (w/v) polyethylene glycol) and appropriate medium. The resulting suspension is centrifuged and the cell pellet resuspended in HAT medium, and seeded in 96-well plates at 100 µl/well ($2.5\times10^5$ cells/well) and cultured in a $CO_2$ incubator. On the day after fusion, 100 µl of fresh HAT medium containing 500 µg/ml geneticin (Invitrogen) is added. On days 4 and 7, half of the spent medium is replaced by fresh HAT medium containing 250 µg/ml geneticin. On day 8, the growth of the hybridoma in each well is checked under a microscope. mAb production in culture supernatants can be assayed on day 10 by ELISA assay or days 9 and 10 by FACS sorter. Positive clones can be expanded and the specific hybridomas cloned by a limiting dilution method.

In addition, protocols for producing humanized forms of monoclonal antibodies and fragments of monoclonal antibodies are known in the art (see, e.g., U.S. Pat. Nos. 6,054,297, 6,407,213, 6,639,055, 6,800,738, and 6,719,971 and U.S. Pat. Appl. Pub. Nos. 2005/0033031, and 2004/0236078). Similarly, methods for producing single chain antibodies have been described and can be useful for the making of TAM receptor inhibitors (see, Buchner et al., *Anal. Biochem.* 205: 263-270, 1992; Pluckthun, *Biotechnology* 9:545, 1991; Huse et al., *Science* 246:1275, 1989 and Ward et al., *Nature* 341: 544, 1989).

3. Inhibitory RNA Molecules (RNAi)

In yet another example, TAM receptor inhibitors are siRNAs or other inhibitory RNAs (RNAi) that can decrease or eliminate the biological activity of a TAM receptor, for example by decreasing translation of a TAM receptor or by decreasing TAM receptor ligand levels in the cell. One of ordinary skill in the art can readily generate siRNAs, which specifically bind to a nucleic acid encoding a TAM receptor (e.g., Tyro3, Axl, or Mer) or ligand thereof (e.g., Gas6 or Protein S). As described herein, such sequences are publicly available. In an example, commercially available kits, such as siRNA molecule synthesizing kits from PROMEGA® (Madison, Wis.) or AMBION® (Austin, Tex.) may be used to synthesize siRNA molecules. In another example, siRNAs are obtained from commercial sources, such as from QIAGEN® Inc (Germantown, Md.), INVITROGEN® (Carlsbad, Calif.), AMBION (Austin, Tex.), DHARMACON® (Lafayette, Colo.), SIGMA-ALDRICH® (Saint Louis, Mo.) or OPENBIOSYSTEMS® (Huntsville, Ala.).

siRNAs are double stranded RNAs (dsRNAs) that can induce gene-specific inhibition of expression are provided. These RNAs are suitable for interference or inhibition of expression of a target TAM receptor and comprise double stranded RNAs of about 15 to about 40 nucleotides (such as 19 to 23 nucleotides) containing a 3' and/or 5' overhang on each strand having a length of 0- to about 5-nucleotides, wherein the sequence of the double stranded RNAs is substantially identical to a portion of a mRNA or transcript of the target TAM receptor or ligand thereof for which interference or inhibition of expression is desired. For example, using TAM receptor nucleic acid sequences known in the art (e.g., see GenBank Accession Nos. NM_006293.2, NM_021913.3, and NM_006343.2 for Tyro3, Axl, and Mer, respectively, sequences of which are herein incorporated by reference for the sequence available on Jul. 24, 2008), or TAM receptor ligand sequences known in the art (e.g., see Genbank™ No: NM_000820.1 for Gas6 and Genbank™ No: NM_000313.1 (as of Jul. 24, 2008).) siRNA sequences specific for such sequences can be generated using routine methods. The double stranded RNAs can be formed from complementary ssRNAs or from a single stranded RNA that forms a hairpin or from expression from a DNA vector.

In addition to native RNA molecules, RNA suitable for inhibiting or interfering with the expression of a TAM receptor or ligand thereof include RNA derivatives and analogs. For example, a non-natural linkage between nucleotide residues can be used, such as a phosphorothioate linkage. The RNA strand can be derivatized with a reactive functional group or a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups. Other useful RNA derivatives incorporate nucleotides having modified carbohydrate moieties, such as 2'-O-alkylated residues or 2'-deoxy-2'-halogenated derivatives. Particular examples of such carbohydrate moieties include 2'-O-methyl ribosyl derivatives and 2'-O-fluoro ribosyl derivatives. The RNA bases may also be modified. Any modified base useful for inhibiting or interfering with the expression of a TAM receptor can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

In certain examples, expression vectors are employed to express at least one siRNA molecule. For example, siRNA molecules can be expressed within cells from eukaryotic promoters. Those skilled in the art will recognize that any nucleic acid can be expressed in eukaryotic cells using the appropriate DNA/RNA vector. The activity of such nucleic acids can be augmented by their release from the primary transcript by an enzymatic nucleic acid (see, for instance, Draper et al., PCT WO 93/23569, and Sullivan et al., PCT WO 94/02595).

In some examples, siRNA molecules are expressed from transcription units (see for example, Couture et al., 1996, TIG 12:510) inserted into DNA or RNA vectors. The recombinant vectors can be DNA plasmids or viral vectors. siRNA expressing viral vectors can be constructed based on, for example, but not limited to, adeno-associated virus, retrovirus, adenovirus, lentivirus or alphavirus. In another example, pol III based constructs are used to express siRNA nucleic acid molecules (see, for example, Thompson, U.S. Pat. Nos. 5,902,880 and 6,146,886).

In another example, an expression vector includes a nucleic acid sequence encoding at least one siRNA molecule specifically designed to inhibit expression of a TAM receptor or ligand thereof. In a particular example, the vector contains a sequence(s) encoding both strands of a siRNA molecule comprising a duplex. In another example, the vector also contains sequence(s) encoding a single nucleic acid molecule that is self-complementary and thus forms a siRNA molecule. Once delivered, the recombinant vectors capable of expressing the siRNA molecules persist in target cells. Alternatively, viral vectors can be used that provide for transient expression of nucleic acid molecules. Such vectors can be repeatedly administered as necessary. Once expressed, the siRNA molecule interacts with the TAM receptor mRNA and generates an RNAi response.

4. Aptamers

In yet another example, TAM receptor inhibitors are aptamers that can decrease or eliminate the biological activity of a TAM receptor or ligand thereof. One of ordinary skill in the art can readily generate aptamers specific for a TAM receptor (e.g., Tyro3, Axl, or Mer) or ligand thereof.

Aptamers include single-stranded nucleic acid molecules (such as, DNA or RNA) that assume a specific, sequence-dependent shape and binds to a TAM receptor or ligand thereof with high affinity and specificity. Aptamers generally comprise fewer than 100 nucleotides, fewer than 75 nucleotides, or fewer than 50 nucleotides (such as 10 to 100 or 10 to 50 nucleotides). In another embodiment, a TAM receptor inhibitor is a mirror-image aptamer (also called a SPIEGELMER™). Mirror-image aptamers are high-affinity L-enantiomeric nucleic acids (for example, L-ribose or L-2'-deoxyribose units) that display high resistance to enzymatic degradation compared with D-oligonucleotides (such as, aptamers). The target binding properties of aptamers and minor-image aptamers are designed by an in vitro-selection process starting from a random pool of oligonucleotides, as described for example, in Wlotzka et al., *Proc. Natl. Acad. Sci.* 99(13):8898-902, 2002.

In another example, an aptamer is a peptide aptamer that binds to a TAM receptor or ligand thereof with high affinity and specificity. Peptide aptamers include a peptide loop (e.g., which is specific for a TAM receptor) attached at both ends to a protein scaffold. This double structural constraint greatly increases the binding affinity of the peptide aptamer to levels comparable to an antibody's (nanomolar range). The variable loop length is typically 8 to 20 amino acids (e.g., 8 to 12 amino acids), and the scaffold may be any protein which is stable, soluble, small, and non-toxic (e.g., thioredoxin-A, stefin A triple mutant, green fluorescent protein, eglin C, and cellular transcription factor Sp1). Peptide aptamer selection can be made using different systems, such as the yeast two-hybrid system (e.g., Gal4 yeast-two-hybrid system) or the LexA interaction trap system.

C. Pharmaceutical Compositions

TAM receptor inhibitors used in the methods described herein can be formulated in a variety of ways depending on the location and type of disease to be treated. Pharmaceutical compositions are thus provided for both local (for instance, topical or inhalational) use and for systemic use. Therefore, the disclosure includes within its scope pharmaceutical compositions including at least one TAM receptor inhibitor (e.g., one, two or three TAM receptor inhibitors) formulated for use in human or veterinary medicine. While the TAM receptor inhibitors typically will be used to treat human subjects, they also can be used to treat similar or identical diseases in other vertebrates, such other primates, dogs, cats, horses, and cows.

Pharmaceutical compositions that include at least one TAM receptor inhibitor as described herein as an active ingredient, or that include both a TAM receptor inhibitor and an additional anti-infective agent as active ingredients, can be formulated with an appropriate solid or liquid carrier, depending upon the particular mode of administration chosen. A suitable administration format can best be determined by a medical practitioner for each subject individually. Various pharmaceutically acceptable carriers and their formulation are described in standard formulation treatises, for instance, *Remington's Pharmaceutical Sciences* by E. W. Martin Mack Publishing Co., Easton, Pa., 15th Edition (1975). See also Wang & Hanson (1988) *Journal of Parenteral Science and Technology*, Technical Report No. 10, Supp. 42: 2S.

The dosage form of the pharmaceutical composition is determined by the mode of administration chosen. For instance, in addition to injectable fluids, inhalational, transdermal, rectal, vaginal, and oral formulations can be employed. Inhalational preparations can include aerosols, particulates, and the like. In general, the goal for particle size for inhalation is about 1 μm or less in order that the pharmaceutical reach the alveolar region of the lung for absorption. Oral formulations can be liquid (for instance, syrups, solutions, or suspensions), or solid (for instance, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

In one embodiment, a pharmacological composition is provided that includes at least one TAM receptor inhibitor and a pharmacologically acceptable carrier. Pharmacologically acceptable carriers (for instance, physiologically or pharmaceutically acceptable carriers) are well known in the art. A suitable pharmacological composition can be formulated to facilitate the use of TAM receptor inhibitors in vivo. Such a composition can be suitable for delivery of the active ingredient to any suitable host, such as a patient for medical application, and can be manufactured in a manner that is itself known, for instance, by means of conventional mixing dissolving, granulating, dragee-making, levigating, emulsifying, encapsulating, entrapping, or lyophilizing processes.

The compositions or pharmaceutical compositions can be administered by any route, including parenteral administration, for example, intravenous, intraperitoneal, intramuscular, intraperitoneal, intrathecal, or intra-articular injection or infusion, or by sublingual, oral, topical, rectal, vaginal, intranasal, or transmucosal administration, or by pulmonary inhalation. When TAM receptor inhibitors are provided as parenteral compositions, for instance, for injection or infusion, they are generally suspended in an aqueous carrier, for example, in an isotonic buffer solution at a pH of about 3.0 to about 8.0, for example at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers.

For oral administration, the pharmaceutical compositions that include one or more TAM receptor inhibitors can take the form of, for example, tablets or capsules prepared by conventional means with pharmaceutically acceptable excipients such as binding agents (for instance, pregelatinised maize starch, polyvinyl pyrrolidone or hydroxypropyl methylcellulose); fillers (for instance, lactose, microcrystalline cellulose or calcium hydrogen phosphate); lubricants (for instance, magnesium stearate, talc or silica); disintegrants (for instance, potato starch or sodium starch glycolate); or wetting agents (for instance, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for instance, sorbitol syrup, cellulose derivatives or hydrogenated edible fats); emulsifying agents (for instance, lecithin or acacia); non-aqueous vehicles (for instance, almond oil, oily esters, ethyl alcohol or fractionated vegetable oils); and preservatives (for instance, methyl or propyl-p-hydroxybenzoates or sorbic acid). The preparations can also contain buffer salts, flavoring, coloring, and sweetening agents as appropriate.

For administration by inhalation, the TAM receptor inhibitors for use according to the present disclosure are conveniently delivered in the form of an aerosol spray presentation from pressurized packs or a nebulizer, with the use of a suitable propellant, for instance, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

Pharmaceutical compositions that include at least one TAM receptor inhibitor as described herein as an active ingredient normally will be formulated with an appropriate solid or liquid carrier, depending upon the particular mode of administration chosen. The pharmaceutically acceptable carriers and excipients useful in this disclosure are conventional. For instance, parenteral formulations usually include injectable fluids that are pharmaceutically and physiologically acceptable fluid vehicles such as water, physiological saline, other balanced salt solutions, aqueous dextrose, glycerol or the like. For solid compositions (for instance, powder, pill, tablet, or capsule forms), conventional non-toxic solid carriers can include, for example, pharmaceutical grades of mannitol, lactose, starch, or magnesium stearate. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

D. Use of TAM Receptor Inhibitors to Treat Microbial Infections

Disclosed herein are methods of using one or more TAM receptor inhibitors for treating a microbial infection in a subject. For example administration of a TAM receptor inhibitor to a subject can increase a pro-inflammatory cytokine response, for example an increase in type I IFN production, such as increase in IFN-α or IFN-β production, thereby treating the infection. In particular examples, type I IFN production is increased in an immune cell of the infected subject, such as a macrophage, fibroblast, or DC. For example, type I IFN production (e.g., IFN-α or IFN-β production) can be increased in such cells by at least 20%, for example at least 40%, at least 50%, at least 75%, at least 90%, at least 100%, or at least 200% relative to such production in the absence of the inhibitor. Exemplary subjects that can be treated include mammals, such as humans and veterinary subjects. In some examples, subjects are screened to determine if they have an infection (e.g., bacterial or viral infection) prior to administration of the TAM receptor inhibitor, or screened to see if they have a disease associated with such infection (e.g., AIDS). In some examples, a subject is one who likely has been exposed to a pathogen, and can receive a TAM receptor inhibitor.

The effectiveness of the TAM receptor inhibitor administration can be measured by monitoring one or more symptoms of a disease associated with the infection (e.g., fever, WBC count, vomiting, and the like), monitoring the presence of the pathogen itself (e.g., by determining a viral titer or culturing a biological sample from the subject to determine if the pathogen is still present or has decreased in number), and monitoring type I IFN and/or IRF production, by methods known to one of skill in the art. For example, a decrease in one or more symptoms of the disease, a decrease in viral titer (such as a decrease of at least 20%, at least 40%, at least 50%, at least 75%, at least 90%, or at least 95% relative to viral titer in the absence of the inhibitor), decrease in the number of bacteria (such as a decrease of at least 20%, at least 40%, at least 50%, at least 75%, at least 90%, or at least 95% relative to bacterial numbers in the absence of the inhibitor), an increase in pro-inflammatory cytokine production (such as a increase of at least 20%, at least 40%, at least 50%, at least 75%, at least 90%, at least 100%, or at least 200% relative to such production in the absence of the inhibitor), or an increase in type I IFN and/or IRF production (such as a increase of at least 20%, at least 40%, at least 50%, at least 75%, at least 90%, at least 100%, or at least 200% relative to such production in the absence of the inhibitor), is an indicator of efficacy of TAM receptor inhibitor treatment.

Subjects to be treated may be acutely or chronically infected. For example, a chronic infection can be one where a subject continues to harbor a pathogenic organism but may suffer no ill-effects themselves (e.g., *Salmonella typhi* in the gut and *Corynebacterium diphtheriae* in the respiratory tract), or suffer low-level damage (e.g., a hepatitis B infection). Such an infection can be caused by viruses, whether enveloped or not (e.g., Cytomegalovirus (CMV), hepatitis, herpes simplex (HSV, genital herpes), herpes zoster (HZV, shingles), human papilloma virus (HPV, genital warts, cervical cancer)), HIV (AIDS), HCV (Hepatitis), Coxsackie (Myocarditis), Rhinovirus (Cold), West Nile Virus (Encephalitis), Influenza (Flu)), pathogenic bacteria, such as gram-negative and gram-positive bacteria as well as anaerobic bacteria (e.g., *Mycobacterium* (Tuberculosis), *Listeria*), fungi, or parasites (e.g., *Plasmodium* (malaria)). Other specific examples are provided herein and are known in the art. In some examples, the subject is infected with more than one type of pathogen that can be treated by the disclosed methods.

In some embodiments, the subject is infected with a virus, and may have a chronic viral infection, and may have a disease associated with such infection. Examples of viral infections that can be treated with the methods provided herein include but are not limited to: enveloped or non-enveloped viruses such as members of the following viral families: Retroviridae (e.g., HIV (such as HIV1 and HIV2), MLV, SIV, FIV, Human T-cell leukemia viruses 1 and 2, XMRV, and Coltiviruses (such as CTFV or Banna virus)); Togaviridae (for example, alphaviruses (such as Ross River virus, Sindbis virus, Semliki Forest Virus, O' nyong'nyong virus, Chikungunya virus, Eastern equine encephalitis virus, Western equine encephalitis virus, Venezuelan equine encephalitis virus) or rubella viruses); Flaviridae (for example, dengue viruses, encephalitis viruses (such as West Nile virus or Japanese encephalitis virus), yellow fever viruses); Coronaviridae (for example, coronaviruses such as SARS virus or Toroviruses); Rhabdoviridae (for example, vesicular stomatitis viruses, rabies viruses); Paramyxoviridae (for example, parainfluenza viruses, mumps virus, measles virus, respiratory syncytial virus, sendai virus, and metopneumovirus); Orthomyxoviridae (for example, influenza viruses); Bunyaviridae (for example, Hantaan virus, bunya viruses (such as La Crosse virus), phleboviruses, and Nairo viruses); Hepadnaviridae (Hepatitis B viruses); Herpesviridae (herpes simplex virus (HSV) 1 and HSV-2, varicella zoster virus, cytomegalovirus (CMV), HHV-8, HHV-6, HHV-7, and pseudorabies virus); Filoviridae (filoviruses including Ebola virus and Marburg virus) and Poxyiridae (variola viruses, vaccinia viruses, pox viruses (such as small pox, monkey pox, and Molluscum contagiosum virus), yatabox virus (such as Tanapox and Yabapox)). Non-enveloped viruses can also be treated with the methods provided herein, such as members of the following families: Calciviridae (such as strains that cause gastroenteritis); Arenaviridae (hemorrhagic fever viruses such as LCMV, Lassa, Junin, Machupo and Guanarito viruses); Reoviridae (for instance, reoviruses, orbiviruses and rotaviruses); Birnaviridae; Parvoviridae (parvoviruses, such as Human bocavirus adeno-associated virus); Papillomaviridae (such as papillomaviruses); Papovaviridae (papilloma viruses, polyoma viruses); Adenoviridae (adenoviruses); Picornaviridae (enteroviruses, enteric viruses, Poliovirus, coxsackieviruses, hepatoviruses, cardioviruses, aptoviruses, echoviruses, hepatitis A virus, Foot and mouth disease virus, and rhinovirus) and Iridoviridae (such as African swine fever virus). Other viruses that can be treated using the methods provided herein include unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (for instance, Hepatitis C); calciviruses (such as Norovirus, Norwalk and related viruses); Hepeviruses (such as Hepatitis E, JC and BK viruses) and astroviruses).

In some embodiments, the subject is infected with a lentivirus. Lentiviruses include, but are not limited to human immunodeficiency virus type 1 (HIV-1), human immunodeficiency virus type 2 (HIV-2), simian immunodeficiency virus agm (SIVagm), simian immunodeficiency virus mnd (SIVmnd), simian immunodeficiency virus syk (SIVsyk), simian immunodeficiency virus col (SIVcol), Visna-Maedi virus (VMV), bovine immunodeficiency virus (BIV), feline immunodeficiency virus (FIV), caprine arthritis-encephalitis virus (CAEV), and equine infectious anemia virus (EIAV). In some embodiments, the lentivirus is human immunodeficiency virus type 1 (HIV-1). In some embodiments, the lentivirus is human immunodeficiency virus type 2 (HIV-2). In particular examples, the subject is infected with HIV-1 and may have AIDS or other active disease resulting from the infection.

In some embodiments, the subject is infected with bacteria, and may have a chronic bacterial infection, and may have a disease associated with such infection. Examples of infectious bacteria that can be treated with the methods provided herein include any type of Gram-positive (such as *Streptococcus, Staphylococcus, Corynebacterium, Listeria, Bacillus* and *Clostridium*) or Gram-negative bacteria (such as *Salmonella, Shigella, Enterobacteriaceae, Pseudomonas, Moraxella, Helicobacter, Stenotrophomonas, Bdellovibrio*, acetic acid bacteria, and alpha-proteobacteria), *Escherichia coli, Neisseria gonorrhoeae, Neisseria meningitidis, Moraxella catarrhalis, Hemophilus influenzae, Klebsiella pneumoniae, Legionella pneumophila, Pseudomonas aeruginosa, Proteus mirabilis, Enterobacter cloacae, Serratia marcescens*). Exemplary infectious bacteria include, but are not limited to: *Helicobacter pyloris, Borelia burgdorferi, Legionella pneumophilia, Mycobacteria* sps (such as *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelii*.

In some embodiments, the subject is infected with a fungus, and may have a chronic fungal infection, and may have a disease associated with such infection. Examples of fungal infections that can be treated with the methods provided herein include but are not limited to: aspergillosis, candidiasis (thrush, yeast infection), coccidioidomycosis, cryptococcal meningitis, or histoplasmosis.

In some embodiments, the subject is infected with a parasite, and may have a chronic parasite infection, and may have a disease associated with such infection. Examples of protozoal infections that can be treated with the methods provided herein include but are not limited to: cryptosporidiosis, isosporiasis, microsporidiosis, *Pneumocystis Carinii* pneumonia (PCP), *plasmodium falciparium*, or toxoplasmosis.

In order to increase a type I IFN response to an infection in a subject, a therapeutically effective amount of one or more TAM receptor inhibitors (alone or in combination with other agents) is administered to the subject. An effective amount of a TAM receptor inhibitor can be administered in a single dose, or in multiple doses. For example, in some embodiments, a TAM receptor inhibitor is administered periodically after the initial administration, for example, twice a day or more. In other embodiments, a TAM receptor inhibitor is administered as a continuous infusion. TAM receptor inhibitors can be injected once, for example, or they can be injected in divided doses two or more times, for example monthly, weekly, daily, or 2-4 or more times daily.

In some examples, TAM receptor inhibitors are administered for short periods of time, to decrease undesired side effects that may result from such long-term administration. Therefore, in particular examples, TAM receptor inhibitors are administered for a period of no more than 30 days, no more than 14 days, no more than 7 days, or no more than 3 days, such as a period of 1-30 days, 1-14 days, 1-5 days, 7-14 days, or 3-7 days. In other examples, TAM receptor inhibitors are administered for longer periods of time, but under conditions that decrease undesired side effects that may result from such long-term administration. Therefore, in particular examples, TAM receptor inhibitors are administered at a dose below the $IC_{50}$ of the inhibitor, such as a dose that is at least 10%, at least 25%, at least 40%, at least 60% or at least 80% less than the $IC_{50}$ for the inhibitor, for example, for a period of at least 30 days, at least 60 days, at least 120 days, or at least 365 days, such as a period of 30 to 120 days, 30 to 200 days, or indefinitely.

In one embodiment, the TAM receptor inhibitor can be administered locally, such as by topical application or intradermal administration. In other embodiments, the administration of the TAM receptor inhibitor is systemic. In one embodiment, the TAM receptor inhibitor is administered systemically, such as by intravenous injection, intramuscular injection, or subcutaneous injection. Oral, intravenous, intra-arterial, subcutaneous, intra-peritoneal, intra-muscular, inhalational, and even rectal or vaginal administration is contemplated.

The dosage for a TAM receptor inhibitor may vary depending on the particular TAM receptor inhibitor, mode of administration, condition of the subject, age of the subject, or weight of the subject. However, appropriate dosages can be determined by a skilled clinician. In particular examples, a TAM receptor inhibitor is administered at 0.001 mg/kg to 100 mg/kg for a 70 kg mammal, such as 0.01 to 50 mg/kg, or 1 to 25 mg/kg. In another particular example, a therapeutically effective amount of a TAM receptor inhibitor is 0.001 µg/kg to 100 µg/kg for a 70 kg mammal, such as 0.01 to 50 µg/kg, or 1 to 25 µg/kg. In a specific example, a TAM receptor inhibitor is administered at a dose of about 50 to 1000 mg/day for adult patients, such as about 100 to 800 mg/day, 200 to 600 mg/day, for example 400 or 600 mg/day for adult patients.

In particular embodiments, a TAM receptor inhibitor is administered in conjunction with one or more other anti-infectious agents in therapeutically effective amounts. Administration of the TAM receptor inhibitor can occur prior to administration of the anti-infectious agents, substantially contemporaneously with the anti-infectious agents, or after administration of the anti-infectious agents. Specific, non-limiting examples of suitable anti-infectious agents include anti-fungal compounds, anti-viral compounds, and antibiotics.

Antibiotics include, but are not limited to, amoxicillin, clarithromycin, cefuroxime, cephalexin ciprofloxacin, doxycycline, metronidazole, terbinafine, levofloxacin, nitrofurantoin, tetracycline, and azithromycin. Anti-fungal compounds, include, but are not limited to, clotrimazole, butenafine, butoconazole, ciclopirox, clioquinol, clioquinol, clotrimazole, econazole, fluconazole, flucytosine, griseofulvin, haloprogin, itraconazole, ketoconazole, miconazole, naftifine, nystatin, oxiconazole, sulconazole, terbinafine, terconazole, tioconazole, and tolnaftate. Anti-viral compounds, include, but are not limited to, zidovudine, didanosine, zalcitabine, stavudine, lamivudine, abacavir, tenofovir, nevirapine, delavirdine, efavirenz, saquinavir, ritonavir, indinavir, nelfinavir, saquinavir, amprenavir, and lopinavir. Anti-infectious agents also include hyper-immune globulin. Modes of administration and dosages can be determined by a skilled artisan and are routine.

In some examples, a TAM receptor inhibitor is administered with one or more other agents that stimulate the immune system, such as IFNs, cytokines, interleukins, or other agents that increase cytokine production.

In one embodiment, a combination of TAM receptor inhibitor with one or more agents useful in the treatment of a lentiviral disease is provided. In one specific, non-limiting example, the lentiviral disease is an HIV-1-induced, an HIV-2-induced, a SIV-induced, or a FIV induced disease. Specific, non-limiting examples of antivirals include: AL-721 (from Ethigen of Los Angeles, Calif.), recombinant human interferon beta (from Triton Biosciences of Alameda, Calif.), Acemannan (from Carrington Labs of Irving, Tex.), gangiclovir (from Syntex of Palo Alto, Calif.), didehydrodeoxythymidine or d4T (from Bristol-Myers-Squibb), EL10 (from Elan Corp. of Gainesville, Ga.), dideoxycytidine or ddC (from Hoffman-LaRoche), Novapren (from Novaferon Labs, Inc. of Akron, Ohio), zidovudine or AZT (from Burroughs Wellcome), ribavirin (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others.

Specific, non-limiting examples of immuno-modulators are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG (from Imreg of New Orleans, La.), SK&F106528, TNF (Genentech), and soluble TNF receptors (Immunex).

Specific, non-limiting examples of some anti-infectious agents used include clindamycin with primaquine (from Upjohn, for the treatment of *pneumocystis* pneumonia), fluconazlone (from Pfizer for the treatment of cryptococcal meningitis or candidiasis), nystatin, pentamidine, trimethaprim-sulfamethoxazole, and many others, as described above.

"Highly active anti-retroviral therapy" or "HAART" refers to a combination of drugs which, when administered in combination, inhibits a retrovirus from replicating or infecting cells better than any of the drugs individually. In one embodiment, the retrovirus is a human immunodeficiency virus. In one example, a TAM receptor inhibitor is administered in conjunction with a highly active anti-retroviral therapy that includes the administration of 3' axido-3-deoxy-thymidine (AZT) in combination with other agents. Specific, non-limiting examples of agents that can be used in combination in HAART for a human immunodeficiency virus are nucleoside analog reverse transcriptase inhibitor drugs (NRTI), non-nucleoside analog reverse transcriptase inhibitor drugs (NNRTI), viral-entry inhibitors, integrase inhibitors, maturation inhibitors and protease inhibitor drugs (PI). One specific, non-limiting example of HAART used to suppress an HIV infection is a combination of indinavir and efavirenz, a NNRTI.

In one embodiment, HAART is a combination of three drugs used for the treatment of an HIV infection, such as the drugs shown in Table 1 below. Examples of three-drug HAART for the treatment of an HIV infection include 1 protease inhibitor from column A plus 2 nucleoside analogs from column B in Table 1. In addition, ritonavir and saquinavir can be used in combination with 1 or 2 nucleoside analogs. As disclosed herein, all of these therapies are enhanced by combining them with administration of TAM receptor inhibitors.

TABLE 1

| Column A | Column B |
| --- | --- |
| indinavir (Crixivan) | AZT/ddI |
| nelfinavir (Viracept) | D4T/ddI |
| ritonavir (Norvir) | AZT/ddC |
| saquinavir (Fortovase) | AZT/3TC |
| ritonavir/saquinavir | D4T/3TC |

In addition, other 3- and 4-drug combinations can reduce HIV to very low levels for sustained periods. The combination therapies that are enhanced by TAM receptor inhibitor administration are not limited to the above examples, but include any effective combination of agents for the treatment of HIV disease (including treatment of AIDS).

E. Methods of Identifying Antimicrobials

Other embodiments include methods of screening test agents for their ability to function as an antimicrobial agent. In one embodiment, the method includes contacting a cell expressing a TAM receptor (or a portion thereof, such as one or more receptor binding domains, for instance, the SHBG domain for the ligands and the IgG domains for the receptors, or a transmembrane and intracellular kinase domain) with a pathogen and with one or more test agents, and determining whether the test agent increases type I IFN (e.g., IFN-α or IFN-β) production by the cell or increase production of an IRF (e.g., IRF3, IRF5, or IRF7). In a particular example, the TAM receptor is Tyro3, Axl, or Mer. Detection of increased type I IFN (e.g., IFN-α or IFN-β) or IRF production by the cell in the presence of the test agent (such as an increase of at least 20-fold, 40-fold, 50-fold, or 60-fold) relative to a control level representing type I IFN or IRF production by the infected cells in the absence of the test agent indicates that the test agent is an antimicrobial agent for the tested pathogen. For example, if the cells were infected with influenza and the test agent significant increased type I IFN or IRF production in such cells, this indicates that the test agent is an anti-influenza agent.

1. Cells

Cells that can be used in such an assay include cells that express both a TAM receptor and a cytokine receptor (e.g., type I IFN receptors), such as immune cells that express TAM and type I IFN receptors, for example macrophages and DCs. The TAM receptor and cytokine receptor can be endogenous to the cell or exogenous to the cell (e.g., expressed from a recombinant nucleic acid encoding the protein). In some examples, such cells are primary cells (e.g., directly isolated from a mammalian subject, such as a human or veterinary subject). In other examples, such cells are cell lines, such as those available from American Type Culture Collection, Manassas, Va. (e.g., THP-1). In some examples, the cell has substantially no endogenous TAM receptor. Cells expressing exogenous TAM receptor can be, for example, transiently or stably transfected with an expression vector encoding a TAM receptor polypeptide.

The cells are incubated under conditions that permit the pathogen to enter and infect the cell (e.g., allow bacterial or viral replication). Such methods are routine in the art, and will vary depending on the pathogen. For example, cells can be cultured in an appropriate culture medium at 37° C. In some examples, the cell is infected with the pathogen prior to incubation with the test agent, such as incubation at 37° C. for at least 1 hour, at least 8 hours, at least 12 hours, at least 24 hours, at least 48 hours, or at least 72 hours prior to adding the test agent. Such incubation gives the pathogen time to enter the cells and begin replication prior to adding the test agent. The time points can be selected based on the pathogen used. Cells can be infected with any target pathogen, such as those provided herein. For example, if one wanted to identify an anti-HIV agent, the cells can be infected with HIV (or a HIV pseudotyped virus that included HIV core proteins and the envelope from another virus).

2. Test Agents

The conditions also permit the test agent to interact with (e.g., specifically bind to) a TAM receptor ligand (e.g., Gas6 or ProS), a TAM receptor binding domain (e.g., Tyro3, Axl, or Mer extracellular binding domain), or enter the cell and bind to a Tyro3, Axl, or Mer intracellular kinase domain (e.g., ATP binding site). Exemplary test agents that can be used with such methods include any substance or any combination of substances that is useful for achieving an end or result; for example, a substance or combination of substances useful for increasing type I IFN production (e.g., IFN-α or IFN-β) and/or IFF production to levels useful for treating an infection. Any agent that has potential (whether or not ultimately realized) to modulate any feature of the TAM receptor pathways disclosed herein is contemplated for use in the methods of this disclosure. For example, contemplated are agents that have potential to, in immune cells, increase type I IFN (e.g., IFN-α or IFN-β) mRNA or protein expression, decrease an interaction between a TAM receptor and one of its ligands, decrease an interaction between an intracellular TAM receptor domain and ATP or other regulatory protein that can activate the TAM receptor, or decrease an activity of a TAM receptor.

Exemplary agents include, but are not limited to, peptides such as, for example, soluble peptides, including but not limited to members of random peptide libraries (see, e.g., Lam et al., *Nature*, 354:82-84, 1991; Houghten et al., *Nature*, 354:84-86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang et al., *Cell*, 72:767-778, 1993), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof specific for a TAM receptor or ligand), small organic or inorganic molecules (such as, so-called natural products or members of chemical combinatorial libraries), molecular complexes (such as protein complexes), or nucleic acids (e.g., siRNAs specific for a TAM receptor).

In one example, derivatives of MP470, SGI-AXL-277, AXL-1, AXL-2, AXL-3, AXL-4, AXL-5, AXL-6, AXL-7, AXL-8, or AXL-9 are screened for their ability to increase type I IFN and/or IRF production and thus serve as potential antimicrobial agents. For example, derivatives with one of the following general structures are screened for their ability to increase type I IFN production via inhibiting the intracellular kinase activity of a TAM receptor and thus serve as potential antimicrobial agents:

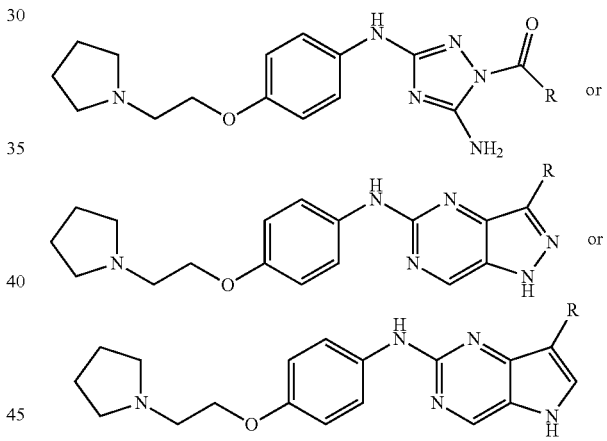

In some examples, the R is H or $CH_3$.

Libraries (such as combinatorial chemical libraries) useful in the disclosed methods include, but are not limited to, peptide libraries (see, e.g., U.S. Pat. No. 5,010,175; Furka, *Int. J. Pept. Prot. Res.*, 37:487-493, 1991; Houghton et al., *Nature*, 354:84-88, 1991; PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Natl. Acad. Sci. USA*, 90:6909-6913, 1993), vinylogous polypeptides (Hagihara et al., *J. Am. Chem. Soc.*, 114:6568, 1992), nonpeptidal peptidomimetics with glucose scaffolding (Hirschmann et al., *J. Am. Chem. Soc.*, 114:9217-9218, 1992), analogous organic syntheses of small compound libraries (Chen et al., *J. Am. Chem. Soc.*, 116:2661, 1994), oligocarbamates (Cho et al., *Science*, 261: 1303, 1003), and/or peptidyl phosphonates (Campbell et al., *J. Org. Chem.*, 59:658, 1994), nucleic acid libraries (see Sambrook et al. *Molecular Cloning, A Laboratory Manual*, Cold Springs Harbor Press, N.Y., 1989; Ausubel et al., *Current Protocols in Molecular Biology*, Green Publishing Associates and Wiley Interscience, N.Y., 1989), peptide nucleic acid libraries (see, e.g., U.S. Pat. No. 5,539,083), antibody libraries (see, e.g., Vaughn et al., *Nat. Biotechnol.*, 14:309-314, 1996; PCT App. No. PCT/US96/10287), carbohydrate libraries (see, e.g., Liang et al., *Science*, 274:1520-1522, 1996; U.S. Pat. No. 5,593,853), small organic molecule libraries (see, e.g., benzodiazepines, Baum, C&EN, Jan. 18, page 33, 1993; isoprenoids, U.S. Pat. No. 5,569,588; thiazolidionones and methathiazones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514) and the like.

Libraries useful for the disclosed screening methods can be produced in a variety of manners including, but not limited to, spatially arrayed multipin peptide synthesis (Geysen, et al., *Proc. Natl. Acad. Sci.*, 81(13):3998-4002, 1984), "tea bag" peptide synthesis (Houghten, *Proc. Natl. Acad. Sci.*, 82(15):5131-5135, 1985), phage display (Scott and Smith, *Science*, 249:386-390, 1990), spot or disc synthesis (Dittrich et al., *Bioorg. Med. Chem. Lett.*, 8(17):2351-2356, 1998), or split and mix solid phase synthesis on beads (Furka et al., *Int. J. Pept. Protein Res.*, 37(6):487-493, 1991; Lam et al., *Chem. Rev.*, 97(2):411-448, 1997).

Libraries may include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

3. Exemplary Assays

In some examples, determining whether the test agent increases type I IFN (e.g., IFN-α or IFN-β) production by the cell includes determining a control level of type I IFN (e.g., IFN-α or IFN-β) production by the infected cell before contacting (e.g., incubating or treating) the cell with the test agent, contacting the infected (or soon to be infected) cell with the test agent, and determining whether contacting the cell with the test agent increases type I IFN (e.g., IFN-α or IFN-β) production by the cell as compared to the control level of type I IFN (e.g., IFN-α or IFN-β) production. In this example, increased type I IFN (e.g., IFN-α or IFN-β) production by the cell in the presence of the test agent (such as an increase of at least 20-fold, 40-fold, 50-fold, or 60-fold) relative to the control level indicates that the test agent is an antimicrobial agent for the tested pathogen. In some examples, IRF production is also assayed, wherein increases in IRF production by the cell in the presence of the test agent (such as an increase of at least 20-fold, 40-fold, 50-fold, or 60-fold) relative to the control level indicates that the test agent is an antimicrobial agent.

In other examples, determining whether the test agent increases type I IFN (e.g., IFN-α or IFN-β) production by the cell includes contacting the infected cell with the test agent, measuring and in some examples quantifying type I IFN produced by the cell, comparing the type I IFN produced to a control or reference value (or range of values expected for a particular condition), and determining whether contacting the cell with the test agent increases type I IFN (e.g., IFN-α or IFN-β) production by the cell. For example, if the amount of type I IFN produced by the cell is substantially increased relative to a control or reference value for type I IFN production by the same cell in the absence of the test agent, this indicates that the agent is an antimicrobial agent for the pathogen tested. In this example, increased type I IFN (e.g., IFN-α or IFN-β) production by the cell in the presence of the test agent (such as an increase of at least 20-fold, 40-fold, 50-fold, or 60-fold) relative to the control level indicates that the test agent is an antimicrobial agent for the pathogen tested. Similarly, if the amount of type I IFN produced by the cell is substantially similar or increased relative to a control or reference value for type I IFN production by the same cell in the presence of a known antimicrobial agent, this indicates that the test agent is an antimicrobial agent. Alternatively, if the amount of type I IFN produced by the cell is substantially similar relative to a control or reference value for type I IFN production by the same cell in the absence of the test agent or known antimicrobial, this indicates that the test agent is not an antimicrobial agent. In some examples, IRF production is also assayed and compared to an IRF control as described for type I IFN.

In one convenient embodiment, high throughput screening methods involve providing a combinatorial chemical or peptide library containing a large number of potential therapeutic compounds (e.g., antimicrobials). Such combinatorial libraries are then screened in one or more assays as described herein to identify those library members (particularly chemical species or subclasses) that display a desired characteristic activity (such as, increasing type I IFN (e.g., IFN-α or IFN-β) and/or IRF mRNA or protein expression (such as an increase of at least 20%, at least 50%, at least 80%, or at least 95% relative to the absence of the test agent), decreasing an interaction between a TAM receptor and one of its ligands (such as a decrease of at least 20%, at least 50%, at least 80%, or at least 95% relative to the absence of the test agent), decreasing an interaction between an intracellular TAM receptor domain and ATP or other regulatory protein that can activate the TAM receptor (such as a decrease of at least 20%, at least 50%, at least 80%, or at least 95% relative to the absence of the test agent), or decreasing an activity of a TAM receptor (such as a decrease of at least 20%, at least 50%, at least 80%, or at least 95% relative to the absence of the test agent)). The compounds thus identified can serve as conventional "lead compounds" or can themselves be used as potential or actual therapeutics. In some instances, pools of candidate agents may be identified and further screened to determine which individual or subpools of agents in the collective have a desired activity.

In some cell-based method embodiments described here and throughout the specification, test cells or test agents can be presented in a manner suitable for high-throughput screening; for example, one or a plurality of test cells can be seeded into wells of a microtitre plate, and one or a plurality of test agents can be added to the wells of the microtitre plate. Alternatively, one or a plurality of test agents can be presented in a high-throughput format, such as in wells of microtitre plate (either in solution or adhered to the surface of the plate), and contacted with one or a plurality of test cells under conditions that, at least, sustain the test cells. Test agents can be added to test cells at any concentration that is not toxic to the cells. It is expected that different test agents will have different effective concentrations. Thus, in some methods, it is advantageous to test a range of test agent concentrations. Expression of a type I IFN-encoding nucleic acid (such as, an IFN-α or IFN-β gene or transcript) or polypeptide (as well as IRF nucleic acids and peptides) can be measured by any method known in the art. For example, the absolute or relative levels of a type I IFN or IRF transcript or polypeptide can be measured by standard techniques, such as, for RNA, Northern blot, PCR (including RT-PCR or q-PCR), in situ hybridization, or nucleic acid microarray, or, for protein, Western blot, antibody array, or immunohistochemistry. In some methods, the expression of a type I IFN or IRF mRNA can also be increased by increased stability of the mRNA. In particular methods, the expression of a type I IFN-encoding nucleic acid (such as, an IFN-α or IFN-β gene or transcript) or polypeptide (or IRF nucleic acid or peptide) is increased when its level or activity is at least 10%, at least 20%, at least 30%, at least 50%, at least 100% or at least 250% higher than control measurements of the same indicator (e.g., in the same test system prior to addition of a test agent, or in a comparable test system in the absence of a test agent).

In some examples, type I IFN production or IRF is assayed by detecting a change (e.g., an increase) in the expression of a type I IFN- (e.g., IFN-α or IFN-β) or IRF- (e.g., IRF3, IRF5, or IRF) encoding nucleic acid. Expression of a gene or gene product (e.g., transcript or protein) can be determined using any expression system capable of expressing a type I IFN (e.g., IFN-α or IFN-β) or IRF polypeptide or transcript (such as, a cell, tissue, or organism, or in vitro transcription or translation systems). In some embodiments, cell-based assays are performed. Non-limiting exemplary cell-based assays may involve test cells such as, cells (including cell lines) that normally express a type I IFN- (e.g., IFN-α or IFN-β) or IRF gene, its corresponding transcript(s) and/or type I IFN- (e.g., IFN-α or IFN-β) or IRF protein(s), or cells (including cell lines) that have been transiently transfected or stably transformed with a reporter construct driven by a regulatory sequence of a type I IFN- (e.g., IFN-α or IFN-β) or IRF gene.

Methods of detecting type I IFNs and IRFs are well known in the art. In one example, cells expressing a TAM receptor are cultured in the presence of a pathogen for 1 to 48 hours and subsequently treated with test media containing the test agent(s), for instance, for 1 to 12 hours (e.g., 4 to 8 hours; 0 hours for a negative control) at 37° C. Type I IFN and/or IRF production is then measured. Cytokine assays are well known in the art. For example, cytokine assays are manufactured by Assay Designs, Inc, Ann Arbor, Mich.; AssayGate, Inc., Ijamsville, Md.; and Panomics, Inc., Fremont, Calif. Exemplary assays include analyzing the supernatant or cells for the presence of a type I IFN (or IRF) using ELISA or analyzing the cell lysate for the presence of type I IFN or IRF nucleic acids using the appropriate primers/probes with qPCR (e.g., qRT-PCR). An increase in Type I IFN or IRF production by the cells incubated in test media relative to the control level of Type I IFN or IRF production by cells not incubated in the test media indicates that the test agent inhibits TAM receptor activity. In some examples, an increase of at least 20-fold, at least 25-fold, at least 35-fold, at least 40-fold, at least 45-fold, or even at least 50-fold relative to a control measurement indicates that the test agent is an antimicrobial (e.g., anti-viral or antibiotic).

Inhibiting TAM receptors to increase type I IFN production has advantageous effects as described herein. Thus, it may be beneficial, in some instances, to further determine whether the effect(s) of an agent identified in some method embodiments is (are) antimicrobial in vivo. Thus, it further may be beneficial (although optional) to further screen agents identified in some method embodiments for their potential to treat or prevent a pathogen infection in a subject; for example, by administering a candidate agent to a subject infected with a pathogen (such as an animal model for the target pathogen, such as a mouse, rat, rabbit, pig, or monkey model) and determining whether the infection is treated by the candidate agent (such as by a decrease in symptoms associated with the infection). Exemplary animal models include a pregnant guinea pig model and mouse model (e.g., see Busch et al., Animal model for infection with *Listeria monocytogenes*. *Curr. Protoc. Immunol.* 2001 May; Chapter 19:Unit 19.9) for *Listeria* monocyotgenes; mice and ferret models for influenza (e.g., see Smee et al., Treatment of influenza A (H1N1) virus infections in mice and ferrets with cyanovirin-N. *Antiviral Res.* E-published 2008 Jul. 2); and a mouse model for *Plasmodium falciparum* malaria (e.g., see Angula-Barturen et al., *PLoS ONE.* 2008 May 21; 3(5):e2252). A candidate agent that decreases infection may be considered as an agent having antimicrobial potential.

The following examples are provided to illustrate certain particular features and/or embodiments. These examples should not be construed to limit the disclosure to the particular features or embodiments described.

EXAMPLES

Example 1

Inhibition of TAM Receptor Activity Decreases Viral Infection

This example describes methods used to demonstrate that inhibition of TAM receptors make cells more resistant to HIV infection. One skilled in the art will appreciate the similar methods can be used to determine the ability of a TAM receptor inhibitor to make cells more resistant to other viral or pathogen infections (e.g., bacteria).

Macrophages from TAM receptor TKO (Tyro3$^{-/-}$, Axl$^{-/-}$ Mer$^{-/-}$ mice see Lu et al., (1999) *Nature* 398, 723-728) or TAM receptor wild-type mice were incubated with Ebola glycoprotein (GP) or VSVg pseudotyped HIV for 24 hours. For making the pseudotyped viruses, 293T cells were seeded in 15 cm plates and transfected with a total of 50 μg (20 μg envelope+30 μg envelope minus HIV provirus) plasmids encoding either the Ebola Zaire envelope glycoprotein (pCB6-EbGP) or the VSV glycoprotein and envelope minus HIV provirus encoding the luciferase reporter gene (NL43R-E-Luc) using Polyethylenimine (PEI, MW 25,000, purchased from Polysciences Inc.) as a transfection reagent. 48 hours post-transfection, the virus in the supernatant was collected, clarified by filtration through 0.45 um pore filter and stored at −80 C.

The viruses were treated with DNAse (40 U/ml of virus) at 37° C. for 1 hour. For heat inactivated virus controls, the virus samples were heated at 95° C. for 1 hour. The MCSF-derived macrophages were plated in 12 well plates and 350 μl virus was added to each well. 24 hours post-infection, the cells were washed with PBS and lysed using 1× lysis buffer. HIV early reverse transcribed (RT) products were measured by q-PCR after 24 hours of viral incubation using the following previously published primers and probe (Munk et al, *PNAS,* 2002. 99(21): 13843-13848): HIVDNA-Early forward primer 5'-GTG CCC GTC TGT TGT GTG AC (SEQ ID NO: 1); HIVDNA-Early reverse primer 5'-GGC GCC ACT GCT AGA GAT TT-3' (SEQ ID NO: 2); and Probe: 5'-(FAM)-CTA GAG ATC CCT CAG ACC CTT TTA GTC AGT GTG G-(TAMRA)-3' (SEQ ID NO: 3). Such products are an indication of viral infection in the cell.

Similar studies were performed with other pseudotyped viruses, including those with an HIV reporter core that carry envelope glycoproteins from murine leukemia virus (MLV) or Marburg virus (MARVGP). The virus stocks were prepared as described above. For Marburg GP pseudotyped virus, the plasmid pWRG7077 encoding Marburg GP of Musoke strain was used, and for MLV-Ampho virus, the MLV-Ampho envelope was used.

Figure 2:
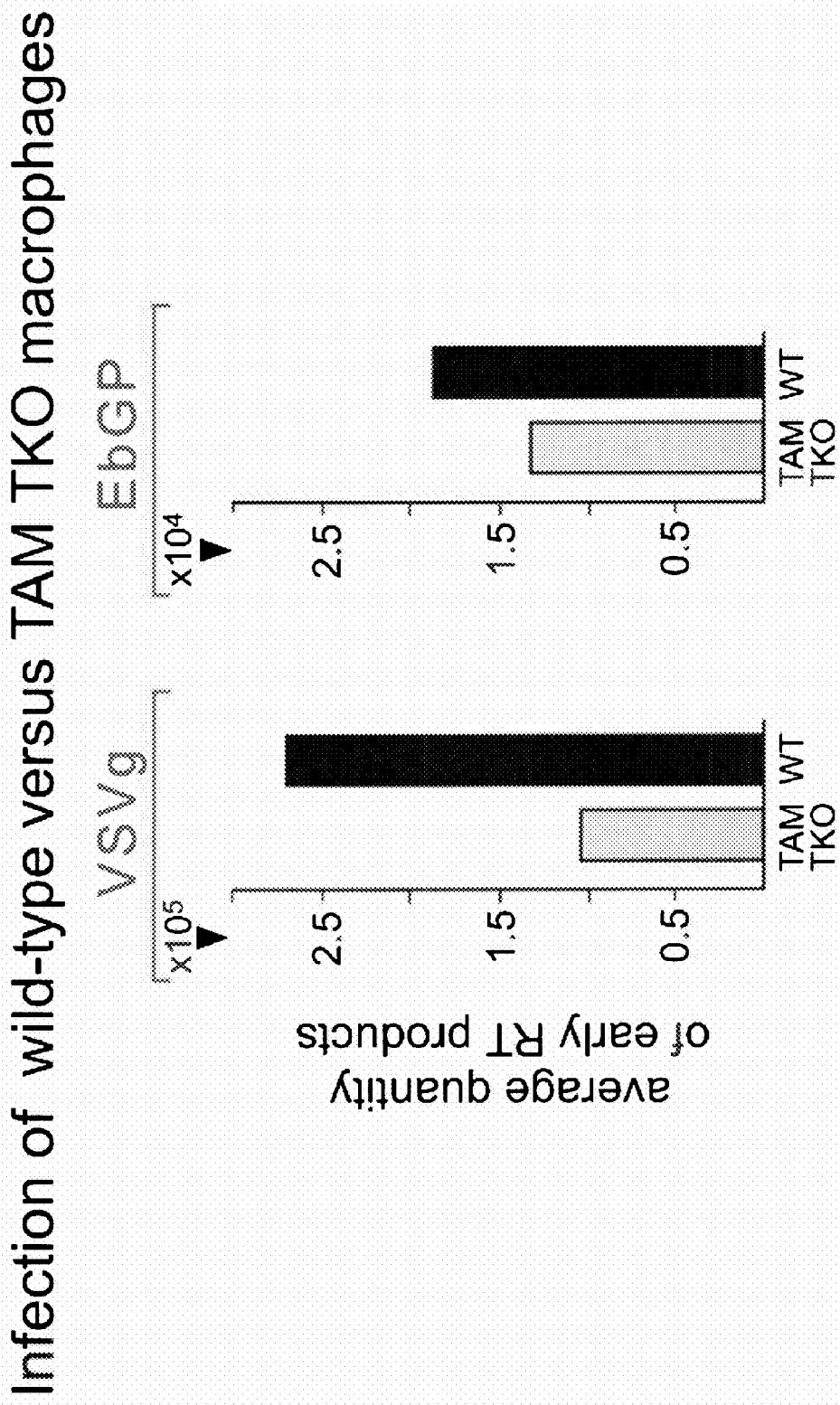
FIG. 2 is a bar graph showing increased infectivity of VSVg (left) and Ebola glycoprotein (GP) (right) pseudotyped viruses in MCSF-derived macrophages from wild-type (WT) mice when compared to TAM triple-knockout mice (TKO).
Figure 4:
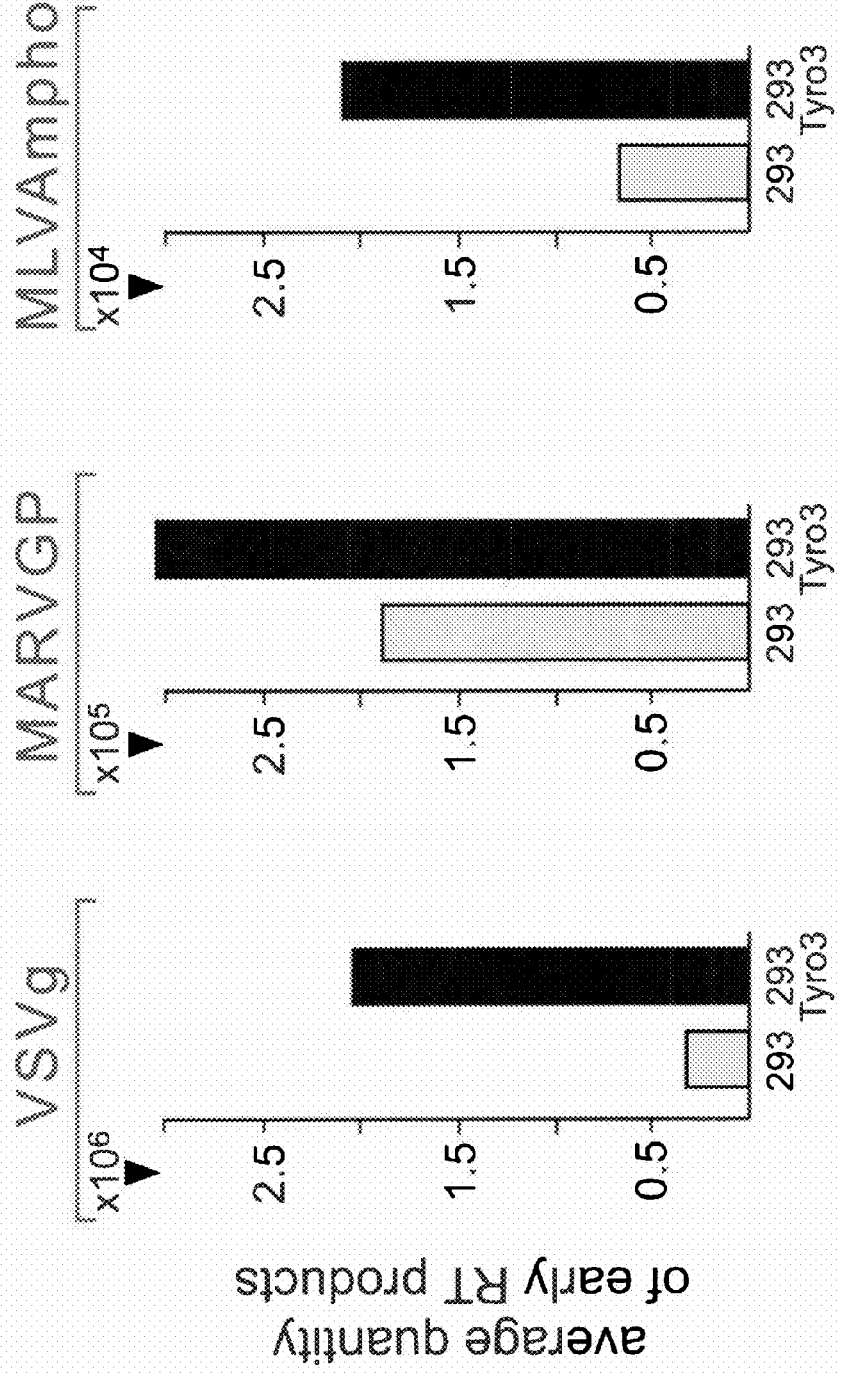
FIG. 4 is a bar graph showing increased viral infectivity in 293 cells stably over-expressing Tyro3 when compared to parental 293 cells. Cells were infected with VSVg-(left), Marburg-virus-glycoprotein-(middle), and MLV-(right) pseudotyped HIV. Early reverse transcription products of the HIV core reporter were measured 24 hours after infection.

As shown in FIG. 2, TAM TKO macrophages are more resistant to viral infection in vitro. In addition, this observation is not specific for the viral envelope indicating that the TAM receptors enhance viral infection at a downstream step post-entry. In addition, as shown in FIG. 4, there was an enhancement of viral infection in 293 cells overexpressing Tyro3 when compared to parental 293 cells, upon infection with pseudotyped viruses (containing an HIV reporter core)

that carry envelope glycoproteins from murine leukemia virus (MLV) or Marburg virus (MARVGP) or vesicular stomatitis virus (VSV).

Example 2

Inhibition of TAM Receptor Expression Enhances Interferon-β Production

This example describes methods used to demonstrate that inhibition of TAM receptors enhances interferon-β (IFN-β) production by the cells challenged with these viruses. One skilled in the art will appreciate that similar methods can be used to determine the ability of a TAM receptor inhibitor to enhance IFN-β production by the cells into which a pathogen (e.g., bacteria) has entered.

Macrophages from TAM receptor TKO or TAM receptor wild-type mice were incubated with VSVg pseudotyped Ebola and VSVg as described in Example 1. IFN-β production by the cells was measured by qPCR after 0 to 8 hours of viral incubation as follows. RNA was isolated with the RNeasy mini kit (QIAGEN). Reverse transcription was performed with RT Superscript III (Invitrogen). PCR reactions were performed on an ABI Prism 7700 Sequence Detection System with SYBRGreen PCR master mix (Applied Biosystems). Each reaction was normalized against the expression of β-actin or GAPDH. Analyses of dissociation curves was performed with SDS software (Applied Biosystems) to control for nonspecific amplification. Primers used to detect IFN-β were: forward, 5'-ATG AGT GGT GGT TGC AGG C-3' (SEQ ID NO: 4) and reverse, 5'-TGA CCT TTC AAA TGC AGT AGA TTC A-3' (SEQ ID NO: 5).

As shown in FIG. 3, enhanced production of IFNβ in TAM TKO macrophages is seen upon challenge of these cells with Ebola and VSVg pseudotyped viruses. Challenge of WT macrophages with pseudotyped viruses carrying Ebola (left panel) or VSV (right panel) envelope glycoproteins leads to 3 and 8-fold elevation in IFNβ, respectively, at 4 hours post-challenge; in marked contrast, challenge of TAM-deficient macrophages with the same viruses results in 55- and 45-fold elevations in IFNβ at 4 hours post-challenge, respectively.

As shown in FIG. 4, when viral infectivity in 293 cells stably over-expressing Tyro3 was compared to parental 293 cells, viral infectivity was much higher in 293 cells stably over-expressing Tyro3. FIG. 4 shows a comparison of Marburg GP, VSVg and MLV Ampho pseudotyped viruses at various time points post-infection. This result confirms that TAM receptors enhance viral infection independent of the viral envelope glycoprotein at a downstream step post-entry.

Example 3

Exemplary Pseudotyped Viruses

This example describes methods that can be used to demonstrate that inhibition of TAM receptors is a pleiotropic antiviral strategy. Although particular pseudotyped viruses are provided, one skilled in the art will recognize that others can be generated and analyzed using similar methods.

Examples 1-2 describe the use of pseudotyped viruses having an HIV core. However, other viruses can be generated using routine methods, such as replication-competent MLV and VSV viruses. Replication-competent VSV virus will be grown in BHK21 cells by a method described previously (Wilson, et al, *Comparative Medicine*, 2008. 58(2): 1-11; herein incorporated by reference as to the method). In the case of MLV, the plasmid encoding GFP-MLV is transfected in 293T cells using PEI as a transfection reagent and 48 h post-transfection the virus in the supernatant is collected, clarified by filtration through 0.45 um pore filter and stored at −80 C. (Sliva, et al, *Virology Journal*, 2004. 1:14).

The resulting viruses are incubated with WT and TAM TKO macrophages as described in the Examples above, and MLV infection can be determined by qPCR using specific primers for MLV RT products. VSV infection can be determined either by plaque assay or by qRTPCR to measure VSV RNA. IFN-β levels can be determined as described in Example 2. By showing that infection of these viruses is also affected by the TAM receptor, this will demonstrate that inhibition of TAM receptors is a pleitropic antiviral strategy.

Example 4

Assessing the IFN Response Profile in WT and TAM TKO Macrophages.

This example provides methods for measuring type I IFN production in wild-type and TAM TKO infected cells.

As described in Example 2 and FIG. 3, challenge of TAM TKO macrophages with various pseudotyped viruses is associated with enhanced production of IFN-β in these cells. To assess the overall interferon response profile, WT and TAM TKO macrophages will be infected with virus as described in Example 1. RNA samples will be collected at different times post-infection and the interferon response profile will be measured employing the mouse Interferon α,β response PCR Array (SuperArray Bioscience Corp.)

Example 5

Measuring Viral Infectivity of WT and TAM TKO Mice in vivo

As described in Examples 1 and 2, TAM TKO macrophages show decreased viral replication and increased IFN-β production in response to challenge with pseudotyped viruses. This example provides methods for determining the susceptibility of WT and TAM TKO mice to viral infections in vivo.

Viral load in the blood of WT and TAM TKO mice will be compared at various time points post-infection with replication-competent MLV and VSV. Morbidity and mortality of the mice will also be monitored. Replication-competent VSV virus will be grown in BHK21 cells by a method described previously (Wilson, et al, *Comparative Medicine*, 2008. 58(2): 1-11). In the case of MLV, the plasmid encoding GFP-MLV is transfected in 293T cells using PEI as a transfection reagent and 48 h post-transfection the virus in the supernatant collected, clarified by filtration through 0.45 um pore filter and stored at −80 C. (Sliva, et al, *Virology Journal*, 2004. 1:14).

MLV viral load can be determined by qPCR using specific primers for MLV RT products. VSV viral load could be measured either by plaque assay or by qRTPCR to measure VSV RNA. It is expected that an increased IFN response and viral clearance will be observed in the TAM TKO mice relative to the TAM WT mice.

While this disclosure has been described with an emphasis upon particular embodiments, it will be obvious to those of ordinary skill in the art that variations of the particular embodiments can be used and it is intended that the disclosure can be practiced otherwise than as specifically described herein. Accordingly, this disclosure includes all modifications encompassed within the spirit and scope of the disclosure as defined by the following claims:

We claimed:

1. A method of treating a subject infected with a pathogen, where said pathogen reduces and/or blocks the natural a type I interferon (IFN) response through activation of TAM receptor signaling, comprising:
   administering to the subject infected with a pathogen a therapeutically effective amount of a TAM receptor inhibitor, thereby treating the subject.

2. The method of claim 1, wherein the TAM receptor is Tyro3, Axl, or Mer.

3. The method of claim 1, wherein the TAM receptor inhibitor is a small molecule.

4. The method of claim 1, wherein the TAM receptor inhibitor is an antibody or antibody fragment thereof.

5. The method of claim 1, wherein the TAM receptor inhibitor binds to an extracellular domain of the TAM receptor, thereby interfering with the binding of Gas6 or Protein S to the TAM receptor and/or activation of the TAM receptor.

6. The method of claim 1, wherein the TAM receptor inhibitor comprises an antibody that binds to Gas6 or Protein S, thereby inhibiting the binding of Gas6 or Protein S to the TAM receptor or activation of the TAM receptor.

7. The method of claim 1, wherein the pathogen is a virus.

8. The method of claim 7, wherein the virus is human immunodeficiency virus (HIV), Hepatitis C virus (HCV), Hepatitis B virus (HBV), West Nile virus, human papillomavirus (HPV), or-Dengue virus.

9. The method of claim 1, wherein the treating includes an increased type I interferon response in the subject.

10. The method of claim 1, wherein the TAM receptor inhibitor inhibits the intracellular kinase domain of the TAM receptor.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer.

<400> SEQUENCE: 1
gtgcccgtct gttgtgtgac                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer.

<400> SEQUENCE: 2
ggcgccactg ctagagattt                                              20

<210> SEQ ID NO 3
<211> LENGTH: 34
<212> TYPE: DNA
<213> ORGANISM: Artificial Sequence
<220> FEATURE:
<223> OTHER INFORMATION: Synthetic oligonucleotide probe.

<400> SEQUENCE: 3
ctagagatcc ctcagaccct tttagtcagt gtgg                              34

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide primer.

<400> SEQUENCE: 4
atgagtggtg gttgcaggc                                               19

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide primer.

<400> SEQUENCE: 5
tgacctttca aatgcagtag attca                                        25